(12) United States Patent
Tanimoto et al.

(10) Patent No.: US 12,426,973 B2
(45) Date of Patent: Sep. 30, 2025

(54) SURGICAL ROBOT AND ROBOTIC SURGICAL SYSTEM

(71) Applicant: KAWASAKI JUKOGYO KABUSHIKI KAISHA, Kobe (JP)

(72) Inventors: Kenichirou Tanimoto, Kobe (JP); Fumiya Matsumoto, Kobe (JP); Tetsuya Nakanishi, Düsseldorf (DE)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 228 days.

(21) Appl. No.: 18/365,268

(22) Filed: Aug. 4, 2023

(65) Prior Publication Data

US 2024/0041549 A1 Feb. 8, 2024

(30) Foreign Application Priority Data

Aug. 5, 2022 (JP) ................. 2022-125756

(51) Int. Cl.
*B25J 9/16* (2006.01)
*A61B 34/00* (2016.01)
*A61B 34/37* (2016.01)
*A61B 90/00* (2016.01)
*A61B 34/30* (2016.01)

(52) U.S. Cl.
CPC .............. *A61B 34/37* (2016.02); *A61B 34/70* (2016.02); *A61B 90/03* (2016.02); *A61B 2034/305* (2016.02)

(58) Field of Classification Search
USPC ................................................ 700/245–264
See application file for complete search history.

(56) References Cited

U.S. PATENT DOCUMENTS

| | | | |
|---|---|---|---|
| 5,710,870 A | 1/1998 | Ohm et al. | |
| 8,280,485 B2* | 10/2012 | Goldenberg | G01R 33/58 600/410 |
| 11,589,935 B2* | 2/2023 | Doi | A61B 34/74 |
| 2013/0053866 A1* | 2/2013 | Leung | B25J 9/1689 901/23 |
| 2018/0146932 A1 | 5/2018 | Suga | |
| 2019/0117310 A1* | 4/2019 | Hiratsuka | B25J 9/1676 |
| 2020/0121403 A1* | 4/2020 | Awano | A61B 34/20 |
| 2020/0170735 A1 | 6/2020 | Yeung et al. | |
| 2020/0212763 A1* | 7/2020 | Takata | A61B 34/30 |
| 2021/0196397 A1* | 7/2021 | Peng | A61B 34/37 |
| 2022/0287784 A1* | 9/2022 | Wakana | A61B 34/37 |

(Continued)

FOREIGN PATENT DOCUMENTS

CN 101862223 A 10/2010
CN 113635343 A 11/2021

(Continued)

*Primary Examiner* — Jonathan L Sample
(74) *Attorney, Agent, or Firm* — METROLEX IP LAW GROUP, PLLC; Robert L. Scott, Esq

(57) ABSTRACT

A surgical robot according to this disclosure includes the joint including an electric motor, a first speed reducer configured to reduce a speed of rotation of the electric motor, and to provide the speed-reduced rotation, a gear part configured to further reduce the speed of the rotation provided from the first speed reducer, and to provide the further-speed-reduced rotation, and a second speed reducer configured to reduce the further-speed-reduced rotation provided from the gear part.

18 Claims, 12 Drawing Sheets

(56) References Cited

U.S. PATENT DOCUMENTS

| | | | | |
|---|---|---|---|---|
| 2022/0378455 A1* | 12/2022 | Takahashi | ............... | A61B 34/37 |
| 2023/0301497 A1* | 9/2023 | Hashimoto | ............... | B25J 18/00 |
| 2023/0310102 A1* | 10/2023 | Xu | ............... | A61B 17/00 |
| | | | | 700/245 |
| 2023/0318514 A1* | 10/2023 | Tanabe | ............... | H02P 29/40 |
| | | | | 318/432 |
| 2024/0041548 A1* | 2/2024 | Tanimoto | ............... | A61B 34/30 |

FOREIGN PATENT DOCUMENTS

| | | | | |
|---|---|---|---|---|
| JP | 2016-516487 A | 6/2016 | | |
| JP | 6457994 B2 | 1/2019 | | |
| JP | 2020-151354 A | 9/2020 | | |
| WO | 2014/146107 A1 | 9/2014 | | |
| WO | WO-2019039131 A1 * | 2/2019 | | |
| WO | WO-2022001224 A1 * | 1/2022 | ............... | A61B 17/00 |

* cited by examiner

|  | 1ST SPEED REDUCER | GEAR PART | 2ND SPEED REDUCER | TOTAL REDUCTION RATIO |
|---|---|---|---|---|
| JT1 | r1 | r3a | r2 | r4a |
| JT2 | r1 | r3b | r2 | r4b |
| JT3 | r1 | r3c | r2 | r4c |
| JT4 | r1 | r3d | r2 | r4d |
| JT5 | r1 | r3e | r2 | r4e |
| JT6 | r1 | r3f | r2 | r4f |

SURGICAL ROBOT AND ROBOTIC SURGICAL SYSTEM

CROSS-REFERENCE TO RELATED APPLICATION

The priority application number JP2022-125756, a surgical robot, Aug. 5, 2022, Kenichirou TANIMOTO, Fumiya MATSUMOTO, and Tetsuya NAKANISHI, upon which this patent application is based, are hereby incorporated by reference.

BACKGROUND OF THE INVENTION

Field of the Invention

This disclosure relates to a surgical robot and a robotic surgical system.

Description of the Background Art

Conventionally, a surgical robot is known. For example, Japanese Laid-Open Patent Publication No. JP 2016-516487 discloses a surgical robot including a manipulator arm. In the Japanese Laid-Open Patent Publication No. JP 2016-516487, a surgical instrument is attached to a free end of the manipulator arm. The manipulator arm includes a plurality of joints. The manipulator arm is configured to translate or rotate the surgical instrument attached to the manipulator arm.

In such a conventional surgical robot disclosed in the Japanese Laid-Open Patent Publication No. JP 2016-516487, a thin manipulator arm is desired for size reduction of the surgical robot, prevention of the manipulator arm from interference with surrounding objects, prevention of manipulator arms from contact with each other, etc.

SUMMARY OF THE INVENTION

The present disclosure is intended to solve the above problem, and provides a surgical robot and a robotic surgical system capable of thinning their robot arm.

In order to attain the aforementioned object, a surgical robot according to a first aspect of the present disclosure includes a robot arm including a free end to which a surgical instrument is attached, and a joint, wherein the joint includes a first speed reducer configured to reduce a speed of rotation of the electric motor, and to provide the speed-reduced rotation, a gear part configured to further reduce the speed of the rotation provided from the first speed reducer, and to provide the further-speed-reduced rotation, and a second speed reducer configured to reduce the further-speed-reduced rotation provided from the gear part.

In the surgical robot according to the first aspect of the present disclosure, as discussed above, the joint includes a first speed reducer configured to reduce a speed of rotation of the electric motor, and to provide the speed-reduced rotation, a gear part configured to further reduce the speed of the rotation provided from the first speed reducer, and to provide the further-speed-reduced rotation, and a second speed reducer configured to reduce the further-speed-reduced rotation provided from the gear part. According to this configuration, because a speed of rotation of the electric motor is reduced by the first speed reducer, the gear part and the second speed reducer as three parts, a total gear ratio of the joint can be large as compared with a case such a joint has one speed reducer. Accordingly, even in a case in which a small electric motor is used, a desired torque to rotate the joint can be provided. Consequently, because the robot arm does not necessarily have a large electric motor, the robot arm can be thinned.

A surgical robot according to a second aspect of the present disclosure includes a robot arm including a fore end to which a surgical instrument is attached, and bending and twisting joints, wherein the joint includes a first electric motor, a first speed reducer configured to reduce a speed of rotation of the first electric motor, and to provide the speed-reduced rotation, a first gear part configured to further reduce the speed of the rotation provided from the first speed reducer, and to provide the further-speed-reduced rotation, and a second speed reducer configured to reduce the further-speed-reduced rotation provided from the first gear part, and the twisting joint includes a second electric motor, a third speed reducer configured to reduce a speed of rotation of the second electric motor, and to provide the speed-reduced rotation, a second gear part configured to further reduce the speed of the rotation provided from the third speed reducer, and to provide the further-speed-reduced rotation, and a fourth speed reducer configured to reduce the further-speed-reduced rotation provided from the second gear part.

In the surgical robot according to the second aspect of the present disclosure, as discussed above, the bending joint includes a first electric motor, a first speed reducer configured to reduce a speed of rotation of the first electric motor, and to provide the speed-reduced rotation, a first gear part configured to further reduce the speed of the rotation provided from the first speed reducer, and to provide the further-speed-reduced rotation, and a second speed reducer configured to reduce the further-speed-reduced rotation provided from the first gear part, and the twisting joint includes a second electric motor, a third speed reducer configured to reduce a speed of rotation of the second electric motor, and to provide the speed-reduced rotation, a second gear part configured to further reduce the speed of the rotation provided from the third speed reducer, and to provide the further-speed-reduced rotation, and a fourth speed reducer configured to reduce the further-speed-reduced rotation provided from the second gear part. According to this configuration, because a speed of rotation of the first electric motor is reduced by the first speed reducer, the first gear part and the second speed reducer as three parts, a total gear ratio of the joint can be large as compared with a case such a joint has one speed reducer. Accordingly, even in a case in which a small electric motor is used as the first electric motor, a desired torque to rotate the joint can be provided. Consequently, because the robot arm does not necessarily have a large electric motor as the first electric motor, the robot arm can be thinned. Also, because the robot arm does not necessarily have a large electric motor as the second electric motor in the twisting joint, the robot arm can be thinned.

A robotic surgical system according to a third aspect of the present disclosure includes a patient-side device including a robot arm that includes a fore end to which a surgical instrument is attached, and a joint; and an operator-side device including an operation unit configured to accept an instruction from an operator, wherein the joint includes an electric motor, a first speed reducer configured to reduce a speed of rotation of the electric motor, and to provide the speed-reduced rotation, a gear part configured to further reduce the speed of the rotation provided from the first speed reducer, and to provide the further-speed-reduced rotation, and a second speed reducer configured to reduce the further-speed-reduced rotation provided from the gear part.

In the robotic surgical system according to the the third aspect of the present disclosure, as discussed above, the joint includes an electric motor, a first speed reducer configured to reduce a speed of rotation of the electric motor, and to provide the speed-reduced rotation, a gear part configured to further reduce the speed of the rotation provided from the first speed reducer, and to provide the further-speed-reduced rotation, and a second speed reducer configured to reduce the further-speed-reduced rotation provided from the gear part. According to this configuration, because a speed of rotation of the electric motor is reduced by the first speed reducer, the gear part and the second speed reducer as three parts, a total gear ratio of the joint can be large as compared with a case such a joint has one speed reducer. Accordingly, even in a case in which a small electric motor is used, a desired torque to rotate the joint can be provided. Consequently, because the robot arm does not necessarily have a large electric motor, the robot arm can be thinned.

According to the present disclosure, robot arm can be thinned.

DESCRIPTION OF THE PREFERRED EMBODIMENT

Configuration of Robotic Surgical System

The following description describes a configuration of a robotic surgical system 100 according to this embodiment. The robotic surgical system 100 includes a surgical robot 1 and a remote control apparatus 2. The remote control apparatus 2 is an example of an operator-side device.

Figure 4:
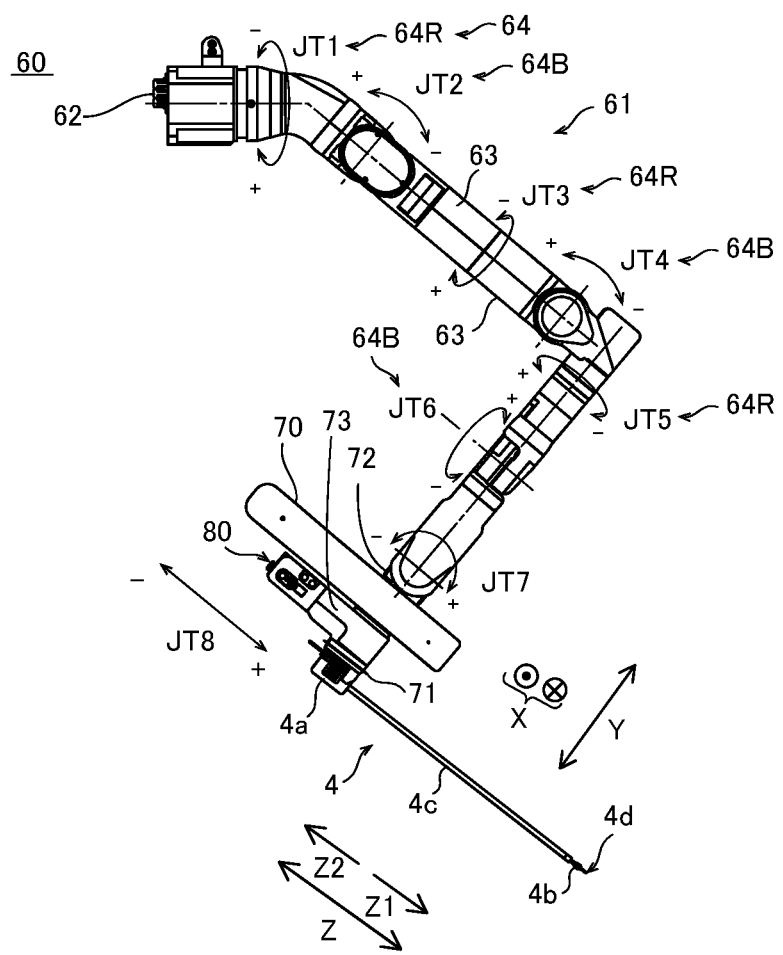
FIG. 4 is a block diagram showing a configuration of a robot arm according to the one embodiment.

In this specification, a longitudinal direction of a surgical instrument 4 is defined as a Z direction as shown in FIG. 4. A free-end side of the surgical instrument 4 is defined as a Z1 side, and a base-end side of the surgical instrument 4 is defined as a Z2 side. A direction orthogonal to the Z direction is defined as an X direction. A direction orthogonal to the Z direction and the X direction is defined as a Y direction.

Figure 3:
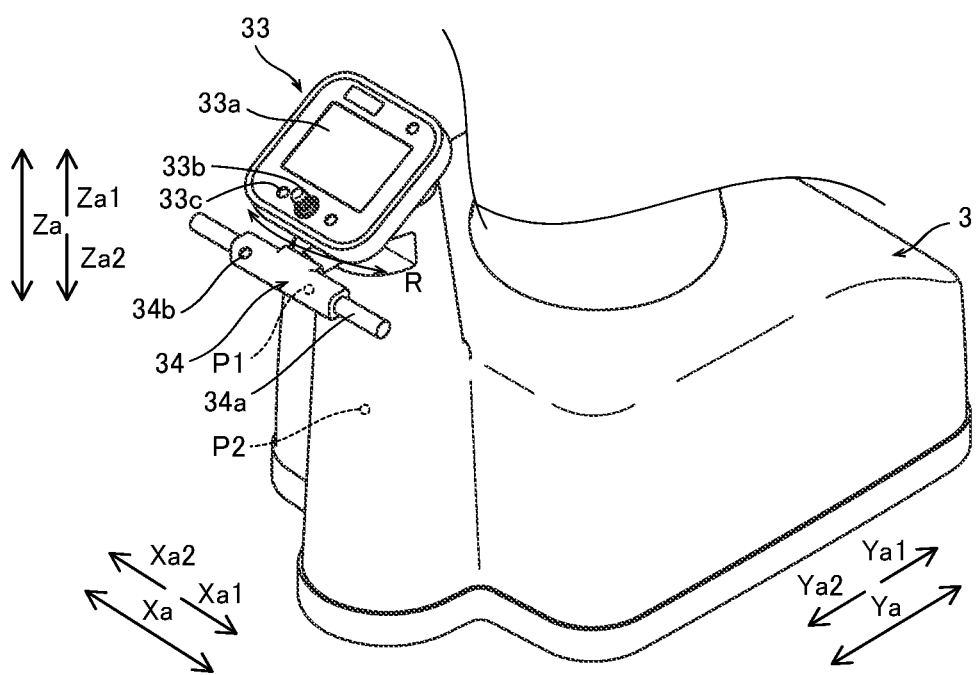
FIG. 3 is a diagram showing a configuration of the medical cart according to the one embodiment.

In this specification, a leftward/rightward direction from the viewpoint of an operator who operates a display 33a of an input device 33 is defined as an Xa direction as shown in FIG. 3. A rightward direction is defined as an Xa1 direction, and a leftward direction is defined as an Xa2 direction. A frontward/rearward direction from the viewpoint of the operator who operates the display 33a of the input device 33 is defined as a Ya direction. A frontward direction is defined as a Ya1 direction, and a rearward direction is defined as a Ya2 direction. A direction orthogonal to a floor on which the surgical robot 1 is arranged is defined as a Za direction. An upward direction is defined as a Za1 direction, and a downward direction is defined as a Za2 direction.

Figure 12:
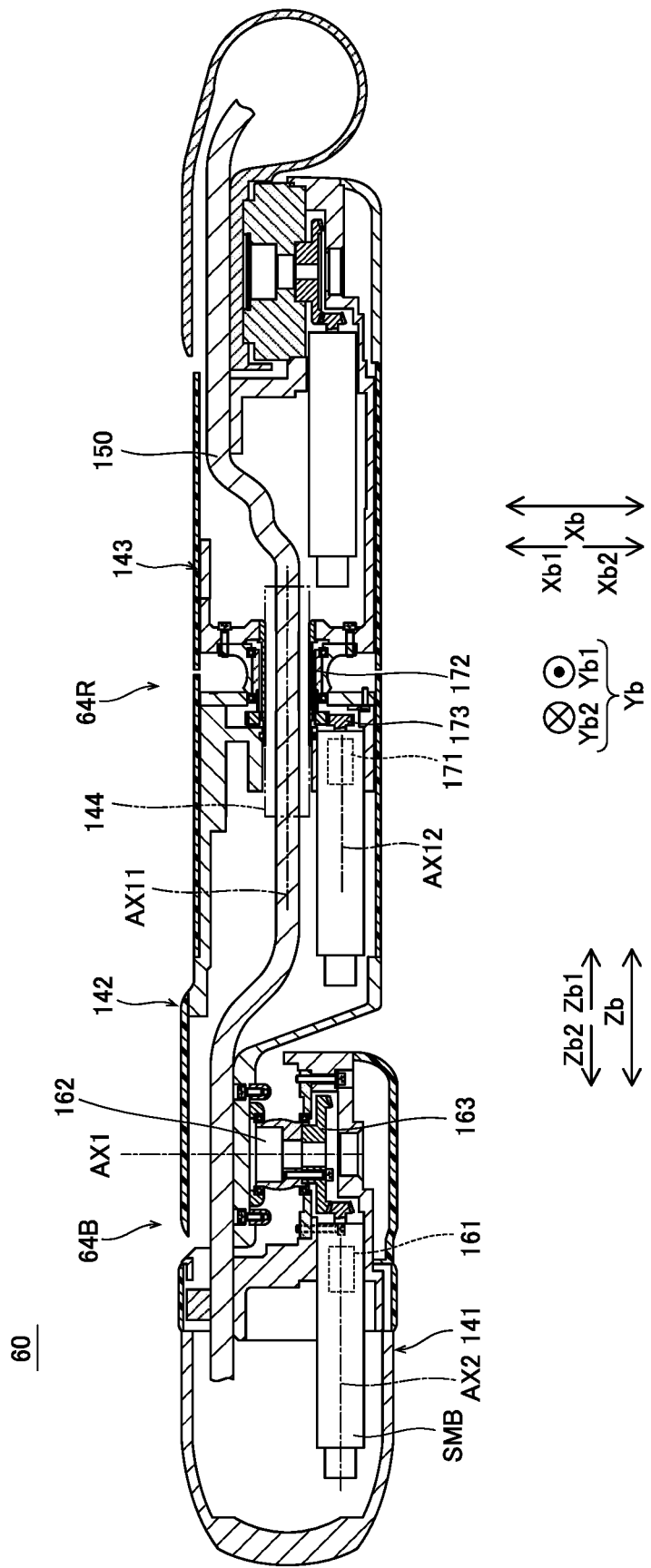
FIG. 12 is a cross-sectional diagram of the robot arm according to the one embodiment as viewed in a Yb direction.

In addition, this specification, as shown in FIG. 12, when a robot arm 60 does not bend, a longitudinal direction of a first housing 141, a second housing 142 and a third housing 143 discussed later is defined as a Zb direction. Also, a longitudinal direction of the robot arm 60 is defined as the Zb direction. As shown in FIG. 12, a direction orthogonal to the Zb direction and extending along a rotation axis AX1 of a joint 64B is defined as an Xb direction. A direction orthogonal to the Zb direction and the Xb direction is defined as a Yb direction.

Figure 1:
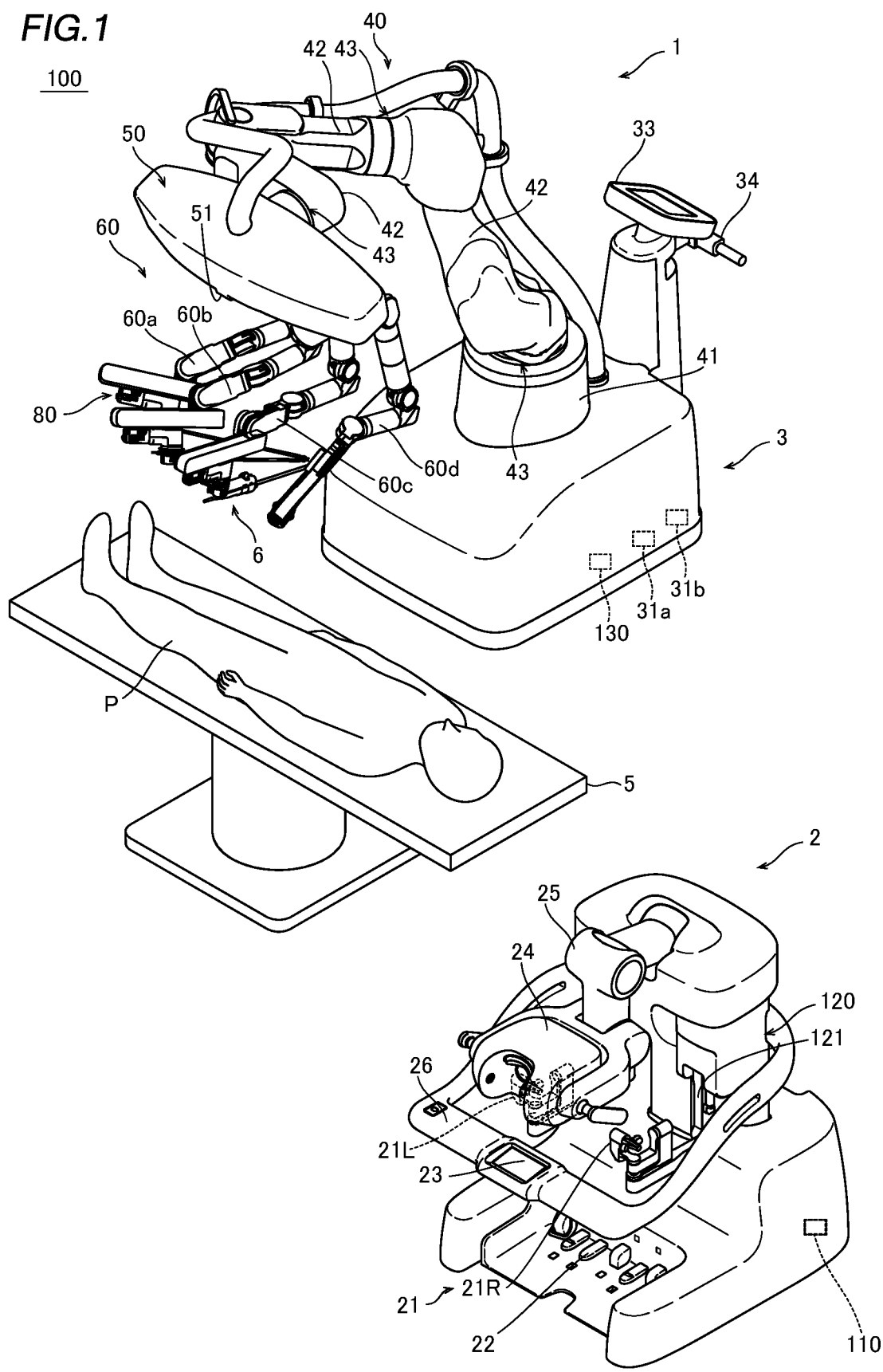
FIG. 1 is a block diagram showing a configuration of a robotic surgical system according to one embodiment.

As shown in FIG. 1, the surgical robot 1 is arranged in an operating room. A remote control apparatus 2 is located remote from the surgical robot 1. An operator, such as a doctor, can provide the remote control apparatus 2 with a command to direct a desired motion of the surgical assistance robot 1. The remote control apparatus 2 transmits the provided command to the surgical robot 1. The surgical robot 1 is configured to perform the motion in accordance with the command received. The surgical robot 1 is arranged in the operating room, which is a sterile field.

Configuration of Surgical Robot

As shown in FIG. 1, the surgical robot 1 includes a medical cart 3, a positioner 40, an arm base 50, a plurality of robot arms 60 and an arm operation unit 80.

As shown in FIG. 3, the medical cart 3 is configured to move the positioner 40. The medical cart 3 includes the input device 33. The input device 33 is configured to accept instructions to move or change orientations of the positioner 40, the arm base 50 and the plurality of robot arms 60 to prepare a surgical operation mainly before the operation is carried out. The medical cart 3 includes an operation handle 34, a stabilizer 34c and an electric cylinder 34d shown in FIG. 9.

Figure 2:
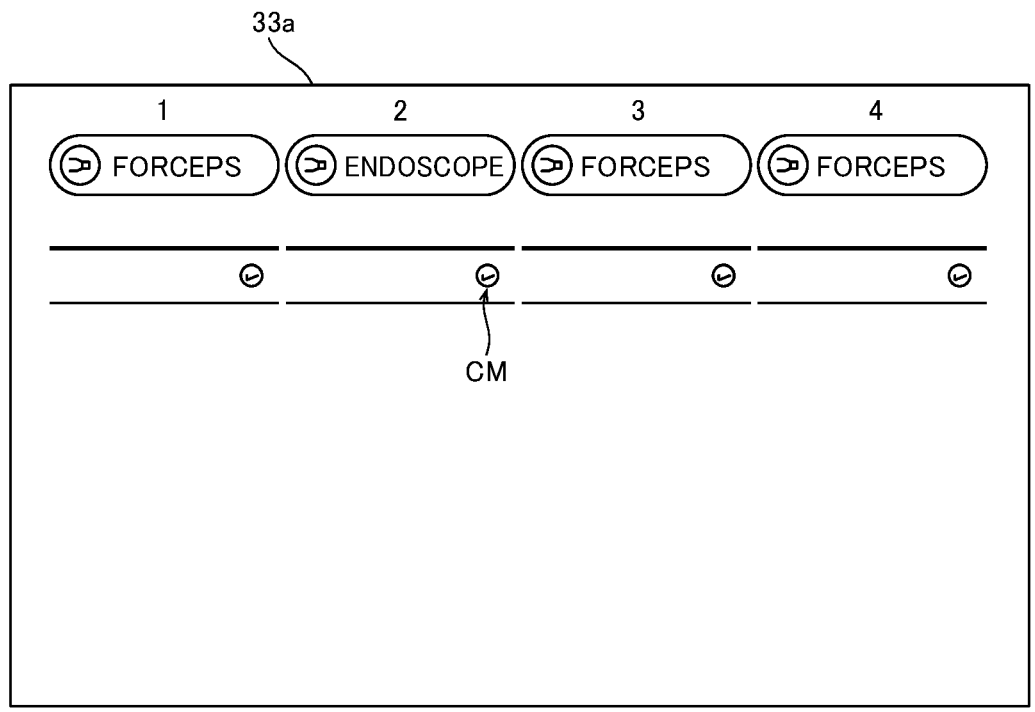
FIG. 2 is a diagram showing a display of a medical cart according to the one embodiment.

As shown in FIG. 2, the input device 33 includes a display 33a, a joystick 33b and an enable switch 33c. For example, the display 33a is a liquid crystal panel. The display 33a indicates numbers corresponding to the plurality of robot arms 60. Also, the display 33a indicates types of surgical instruments 4 attached to the plurality of robot arms 60. The display 33a indicates checkmarks CM representing that their pivot positions PP have been set.

As shown in FIG. 3, the joystick 33b is arranged in proximity to the input device 33 of the medical cart 3. When an operation mode displayed on the input device 33 is selected, the positioner 40 can be three-dimensionally moved by operating the joystick 33b.

The enable switch 33c is arranged in proximity to the joystick 33b of the medical cart 3. The enable switch 33c is configured to enable or disable movement of the positioner 40. When the enable switch 33c is pressed so that movement of the positioner 40 is enabled, the positioner 40 can be moved in accordance with a manual operation of the joystick 33b.

Also, the operation handle 34 is arranged in proximity to the display 33a of the medical cart 3. The operating handle 34 includes a throttle grip 34a that is configured to be gripped and twisted by an operator such as nurse, engineer, etc. to control movement of the medical cart 3. Specifically, the operation handle 34 is arranged under the input device 33. The medical cart 3 can move forward when the throttle grip 34a is twisted from a near side toward a far side. The medical cart 3 can move backward when the throttle grip 34a is twisted from the far side toward the near side. A speed of the medical cart 3 can be changed in accordance with a twisting amount of the throttle grip 34a. In addition, the operation handle 34 is configured to swing leftward and rightward as shown by an R direction, and to rotate the medical cart 3 depending on the swinging operation of the operation handle 34.

Also, the operation handle 34 of the medical cart 3 includes an enable switch 34b configured to enable or disable movement of the medical cart 3. When the enable switch 34b is pressed so that movement of the medical cart 3 is enabled, the medical cart 3 can be moved in accordance with a manual operation of the throttle grip 34a of the operating handle 34.

For example, as shown in FIG. 1, the positioner 40 is constructed of a 7-axis multi-joint robot. The positioner 40 is arranged on the medical cart 3. The positioner 40 is configured to adjust a position of the arm base 50. The positioner 40 can move the position of the arm base 50 in three dimensions.

The positioner 40 includes a base 41, and a plurality of links 42 coupled to the base 41. The links 42 are coupled to each other by joints 43.

The arm base 50 is attached to a free end of the positioner 40. The base ends of the plurality of robot arms are attached to the arm base 50. The plurality of robot arms 60 are foldable into a storage posture. The arm base and the plurality of robot arms 60 covered by sterile drapes when used. The robot arm 60 is configured to support surgical instruments 4.

Figure 9:
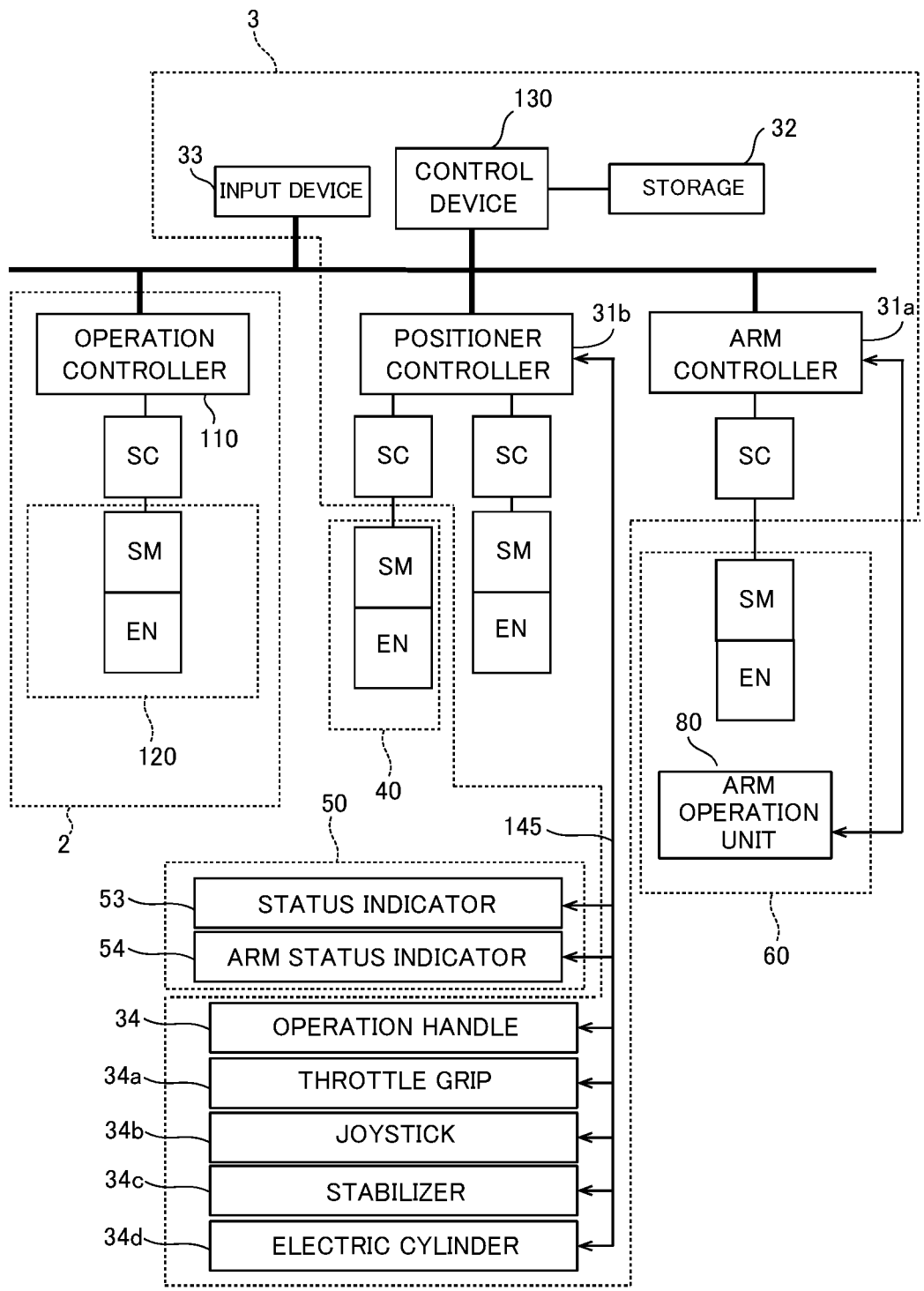
FIG. 9 is a control block diagram of a surgical robot according to the one embodiment.

A status indicator 53 and an arm status indicator 54 shown in FIG. 9 are provided in the arm base 50. The status indicator 53 is configured to indicate a status of robotic surgical system 100. The arm status indicator 54 is configured to indicate states of robot arms 60.

Two or more robot arms 60 are provided as plurality of robot arms 60. Specifically, four robot arms 60a, 60b, 60c and 60d are provided. The robot arms 60a, 60b, 60c and 60d have a similar configuration to each other.

As shown in FIG. 4, each robot arm 60 includes an arm 61, a first link part 72, a second link part 73, a translation mechanism 70, and a joint 64.

The robot arm 60 has JT1, JT2, JT3, JT4, JT5, JT6 and JT7 axes as rotation axes, and a JT8 axis as a linear-motion axis. The axes from JT1 to JT7 are rotation axes of the joint 64 of the arm 61. The JT7 axis is a rotational axis of the first link part 72. The JT8 axis is a linear-motion axis along which the second link part 73 is moved relative to the first link part 72 in the Z direction by the translation mechanism 70. The arm 61 includes a base 62, links 63 and joints 64.

In this embodiment, the joints 64 include joints 64B and joints 64R. The joint 64B is a bending (hinge) joint configured to pivot so that the robot arm 60 can be folded. A rotation axis of joint 64B is referred to as a bend axis. The joints 64 that have the JT2 axis, the JT4 axis, and the JT6 axis as rotation axes are the joint 64B, which is a bending joint. The joint 64R is a twisting joint that rotates about a longitudinal direction of the robot arm 60 as a rotation axis. The rotation axis of the joint 64R is referred to as a roll axis. The joint 64 that has the JT1 axis, the JT3 axis, and the JT5 axis as rotation axes is the joint 64R, which is a twisting joint. Structures of the joint 64B and the joint 64R will be described in detail later. The joints 64B and 64R are examples of first and second joints, respectively.

The arm 61 is constructed of a 7-axis multi-joint robot arm. The first link part 72 is arranged in a free end of arm 61. The arm operation unit 80 discussed later is attached to the second link part 73. The translation mechanism 70 is arranged between the first link part 72 and the second link part 73. The second link part 73 includes a holder 71 configured to hold the surgical instrument 4.

Surgical instruments 4 can be attached to the free ends of the plurality of robot arms 60. The surgical instruments 4 include, for example, replaceable instruments, an endoscope 6 configured to capture images of a part to be operated, a pivot-position setting tool 7 to set a pivot position PP described below, etc. The surgical instrument 4 as the instrument includes a driven unit 4a, a forceps 4b and a shaft 4c.

As shown in FIG. 1, an endoscope 6 is attached to the free end of one, e.g., the robot arm 60c of the robot arms and the surgical instruments 4 other than the endoscope 6 are attached to the free ends of the robot arms 60a, 60b and 60d. The endoscope 6 is attached to one of two robot arms 60b and 60c, which are located in a central part, of the four robot arms 60 arranged adjacent to each other.

Configuration of Instrument

Figure 5:
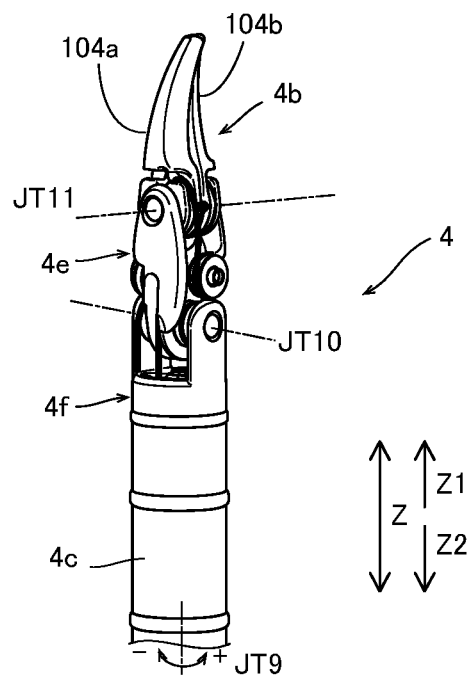
FIG. 5 is a diagram showing a forceps.

For example, as shown in FIG. 5, a forceps 4b is attached to the free end of the instrument. Tools that include a joint and can be attached to the free end of the instrument can include scissors, a grasper, a needle holder, a microdissector, a staple applier, a tucker, a vacuum cleaning tool, a snare wire, a clip applier, etc., other than the forceps 4b. Tools that do not include any joint and can be attached to the free end of the instrument can include a cutting blade, a cautery probe, a cleaner, a catheter, a vacuum orifice, etc.

Forceps 4b includes a first support 4e and a second support 4f. The first support 4e is configured to rotatably support a base end side of jaws 104a and 104b about a JT11 axis. The second support 4f is rotatably configured to support a base-end side of the first support 4e about a JT10 axis. The shaft 4c can rotate about a JT9 axis. The jaws 104a and 104b can pivot about the JT11 axis to open and close.

Configuration of Arm Operation Unit

Figure 6:
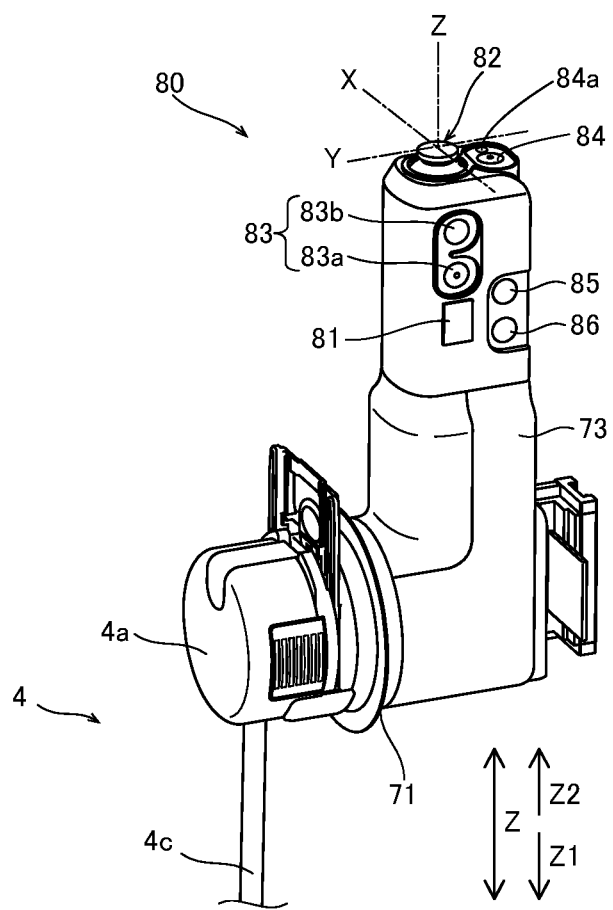
FIG. 6 is a block diagram showing a configuration of an arm operation unit according to the one embodiment.

As shown in FIG. 6, the arm control unit 80 is mounted to the robot arm 60, and is configured to operate the robot arm 60. Specifically, the arm operation unit 80 is mounted to the second link part 73.

The arm control unit 80 includes an enable switch 81, a joystick 82, linear switches 83, a mode switching button 84, a mode indicator 84a, a pivot button 85, and an adjustment button 86.

The enable switch 81 is configured to enable or disable movement of the robot arm 60 by means of the joystick 82 and the linear switches 83. Movement of the surgical instrument 4 by the robot arm 60 is enabled when the enable switch 81 is pressed while the arm operation unit 80 is grasped by an operator such as nurse, assistant, etc.

The joystick 82 is an operation tool configured to control movement of the surgical instrument 4 by the robot arm 60. The joystick 82 is an operation tool configured to control a moving direction and a moving speed of the robot arm 60. The robot arm 60 can be moved in accordance with to a tilting direction and a tilting angle of the joystick 82.

The linear switches 83 are a switch for moving the surgical instrument 4 in the Z direction, which is a longitudinal direction of the instrument 4. The linear switches 83 includes a linear switch 83a for moving the surgical instrument 4 in a direction in which the surgical instrument 4 is inserted into a patient P, and a linear switch 83b for moving the surgical instrument 4 in a direction in which the surgical instrument 4 is moved away from the patient P. The linear switch 83a and the linear switch 83b are constructed of a press-button switch.

Figure 7:
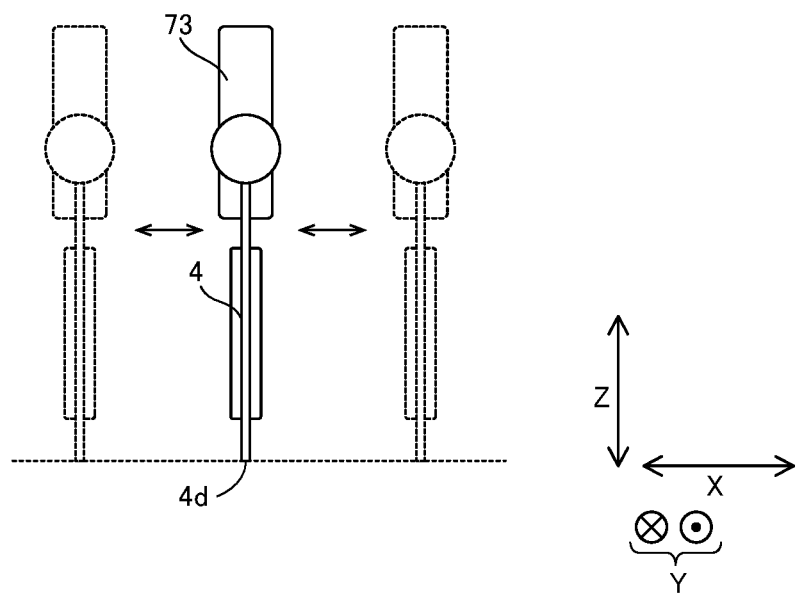
FIG. 7 is a diagram illustrating translational movement of the robot arm.
Figure 8:
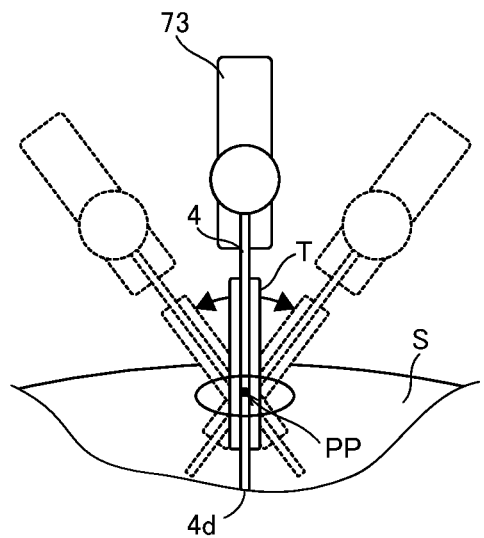
FIG. 8 is a diagram illustrating rotational movement of the robot arm.

The mode switching button 84 is a press-button switch for switching between a translation mode in which the surgical instrument 4 is translationally moved as shown in FIG. 7, and a rotation mode in which the surgical instrument 4 is rotated as shown in FIG. 8. As shown in FIG. 7, in the translation mode in which the robot arm 60 is translationally moved, the robot arm 60 can be moved so that the free end 4d of the surgical instrument 4 can be moved in an X-Y plane. As shown in FIG. 8, in the rotation mode in which the robot arm 60 is rotated, in a case in which any pivot position PP is not stored in the storage 32, the robot arm 60 can be moved so that the forceps 4b can be rotated about a center of the forceps 4b on the JT11 axis, and in a case in which a pivot position PP is stored in the storage 32, the robot arm 60 can be moved so that the forceps 4b can be rotated about the pivot position PP as a rotation axis. In this case, the surgical instrument 4 is rotated with the shaft 4c of the surgical instrument 4 being inserted into a trocar T. The mode switching button 84 is arranged on a surface on a Z-direction side of the arm operation unit 80.

The mode indicator 84a is configured to indicate which mode is selected. The mode indicator 84a is configured to light on to indicate the rotation mode, and to light off indicate the translation mode. The mode indicator 84a also serves as a pivot position indicator to indicate that the pivot position PP is set. The mode indicator 84a is arranged on the surface on the Z-direction side of the arm operation unit 80.

The pivot button 85 is a press-button switch configured to set the pivot position PP, which corresponds to the rotation axis of the surgical instrument 4 attached to the robot arm 60.

The adjustment button 86 is a button configured to optimize a position of the robot arm 60. After the pivot position PP is set with respect to the robot arm 60 to which the endoscope 6 is attached, when the adjustment button 86 is pressed positions of the other robot arms 60 and the arm base 50 is optimized.

Remote Control Apparatus

For example, as shown in FIG. 1, the remote control apparatus 2 is arranged in an operating room or outside the operating room. The remote control apparatus 2 includes operation units 120 including an arm 121 and an operation handle 21, a foot pedal 22, a touch panel 23, a monitor 24, a support arm 25, and a support bar 26. The operation units 120 serve as a handle for operation that is configured to receive commands from an operator such as doctor.

The operation units 120 are a handle configured to manipulate the surgical instrument 4. Also, the operation units 120 are configured to receive manipulated amounts corresponding to the surgical instruments 4. A control device 130 discussed later is configured to control the surgical instrument 4 and the robot arm 60 so that the surgical instruments 4 are moved to desired positions in accordance with the manipulated amounts of the operation unit 120. The operation units 120 include an operation unit 120 that is arranged on a left side from viewpoint of an operator such as doctor and is configured to be manually operated by operator's left hand, and an operation unit 120 that is arranged on a right side from viewpoint of the operator such as doctor and is configured to be manually operated by operator's right hand. The operation unit 120L and the operation unit 120R include an operation handle 21L and an operation handle 21R, respectively.

The monitor 24 is a scope-type display device configured to display images captured by the endoscope 6. The support arm 25 supports the monitor 24, and can adjust a height of the monitor 24 to a height of eyes of the operator such as doctor. The touch panel 23 is arranged on the support bar 26. When a head of the operator is detected by a sensor arranged in proximity to the monitor 24, the surgical robot 1 can accept manual operations from the remote control apparatus 2. The operator will manually operate the operation unit 120 and the foot pedal 22 while seeing of an affected area on the monitor 24. Commands can be provided to the remote control apparatus 2 in accordance with these manual operations. Instructions provided to the remote control apparatus 2 are transmitted to the surgical assistance robot 1.

Configuration of Control System

As shown in FIG. 9, robotic surgical system 100 includes a control device 130, an arm controller 31a, a positioner controller 31b, and an operation controller 110.

The control device 130 is accommodated in the medical cart 3, and configured to communicate with the arm controller 31a and the positioner controller 31b so that the robotic surgical system 100 is entirely controlled. Specifically, the control device 130 is configured to control the arm controller 31a, the positioner controller 31b and the operation controller 110 by using the communications with them. The control device 130 is connected to the arm controller 31a, the positioner controller 31b and the operation controller 110 through LAN, etc. The control unit 130 is arranged in the medical cart 3.

Each of the plurality of robot arms 60 includes the arm controller 31a. In other words, a plurality of arm controllers 31a the number of which corresponds to the number of the plurality of robot arms 60 are included in the medical cart 3.

As shown in FIG. 9, the input device 33 is connected to the control device 130 through LAN, etc. The status indicator 53, the arm status indicator 54, the operation handle 34, the throttle grip 34a, the joystick 33b, the stabilizer 34c and the electric cylinder 34d are connected to the positioner controller 31b through a wire line 145 by means of a communication network that can share information with them by using serial communication. Although all of the status indicator 53, arm status indicator 54, and the like are connected to each other through one wiring line 145 in FIG. 9, wiring lines 145 are actually provided to each of the status indicator 53, the arm status indicator 54, the operation handle 34, the throttle grip 34a, the joystick 33b, the stabilizer 34c and the electric cylinder 34d.

Figure 10:
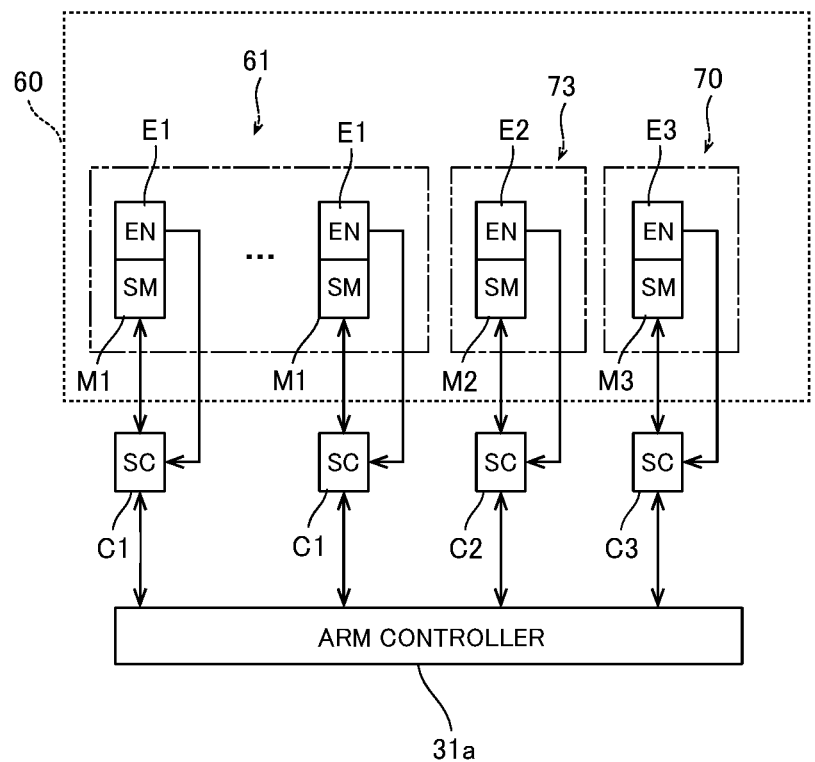
FIG. 10 is a control block diagram of the robot arm according to the one embodiment.

As shown in FIG. 10, each arm 61 includes a plurality of servomotors M1, a plurality of encoders E1 and a plurality of speed reducers corresponding to a plurality of joints 64. The encoder E1 is configured to detect a rotation angle of the servomotor M1. The speed reducer is configured to reduce a rotation of the servomotor M1 whereby increasing its torque. A servo controller C1 is configured to control the servomotor M1, and is arranged in the medical cart 3 adjacent to the arm controller 31a. Also, the encoder E1 is configured to detect the rotation angle of the servomotor M1, and is electrically connected to the servo controller C1.

The second link part 73 includes a servomotor M2 configured to rotate a driven member arranged in a driven unit 4a of the surgical instrument 4, an encoder E2, and a speed reducer. The encoder E2 is configured to detect a rotation angle of the servomotor M2. The speed reducer is configured to reduce a rotation of the servomotor M2 whereby increasing its torque. The medical cart 3 includes a servo controller C2 configured to control the servomotor M2 for driving the surgical instrument 4. The encoder E2 for detecting the rotation angle of the servomotor M2 is electrically connected to the servo control unit C2. Note that a plurality of servomotors M2, a plurality of encoders E2 and a plurality of servo controllers C2 are included.

The translation mechanism 70 includes a servomotor M3 configured to translationally move the surgical instrument 4, an encoder E3, and a speed reducer. The encoder E3 is configured to detect a rotation angle of the servomotor M3. The speed reducer is configured to reduce a rotation of the servomotor M3 whereby increasing its torque. The medical cart 3 includes a servo controller C3 configured to control the servomotor M3 for translationally moving the surgical instrument 4. The encoder E3 for detecting the rotation angle of the servomotor M3 is electrically connected to the servo control unit C3.

Figure 11:
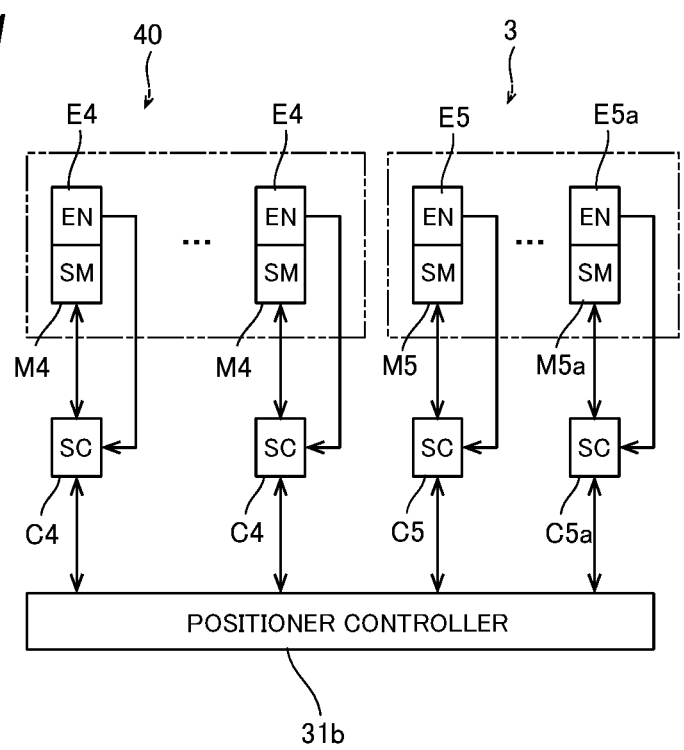
FIG. 11 is a control block diagram of the medical cart and a positioner according to the one embodiment.

As shown in FIG. 11, the positioner 40 includes a plurality of servomotors M4, a plurality of encoders E4 and a plurality of speed reducers corresponding to a plurality of joints 43 of the positioner 40. Each encoder E4 is configured to detect a rotation angle of the servomotor M4. The speed reducer is configured to reduce a rotation of the servomotor M4 whereby increasing its torque.

The medical cart 3 includes front wheels as driving wheels, and rear wheels configured to be steered by manually operating the handle 34. The rear wheels are arranged closer to the operating handle 34 with respect to the front wheels. The medical cart 3 includes a servomotor M5 configured to drive the front wheels of the medical cart 3, an encoder E5, speed reducers, and brakes. The speed reducer is configured to reduce a rotation of the servomotor M5 whereby increasing its torque. Also, the operation handle 34 of the medical cart 3 includes a potentiometer P1 shown in FIG. 3, and the servomotor M5 of the front wheels can be driven in accordance with a rotation angle detected by the potentiometer P1 in response to a twisting amount of the throttle grip 34a. The rear wheels of the medical cart 3 have a twin-wheel type structure, and the rear wheels can be steered in accordance with a rightward/leftward turn of the operating handle 34. Also, the operation handle 34 of the medical cart 3 includes a potentiometer P2 shown in FIG. 3 on a turning shaft, and the rear wheel of medical cart 3 is provided with a servomotor M5a, an encoder E5a, and speed reducers. The speed reducer is configured to reduce a rotation of the servomotor M5a whereby increasing its torque. The servomotor M5a can be driven in accordance with a rotation angle detected by the potentiometer P2 in response to a rightward/leftward turning amount of the operation handle 34. In other words, power is assisted by the servomotor M5a when the rear wheels are steered by turning the operation handle 34 rightward or leftward.

The medical cart 3 can be moved forward or rearward by driving the front wheels. Also, the medical cart 3 can be turned rightward or leftward by steering the rear wheels by turning the operating handle 34 of the medical cart 3.

As shown in FIG. 11, the medical cart 3 includes servo controllers C4 configured to control the servomotors M4 for moving the positioner 40. Also, the encoder E4 is configured to detect the rotation angle of the servomotor M4, and is electrically connected to the servo controller C4. The medical cart 3 includes a servo controller C5 configured to control the servomotor M5 for driving the front wheels of the medical cart 3. The encoder E5 for detecting the rotation angle of the servomotor M5 is electrically connected to the servo control unit C5. The medical cart 3 includes a servo controller C5a configured to control the servomotor M5a for power assistance to steering of the rear wheels of the medical cart 3. The encoder E5a for detecting the rotation angle of the servomotor M5a is electrically connected to the servo control unit C5a.

As shown in FIG. 9, the control device 130 is configured to control the robot arm 60 in accordance with manual operations received by the arm operation unit 80. For example, the control device 130 is configured to control the robot arm 60 in accordance with manual operations received by the joystick 82 of the arm control unit 80. Specifically, the arm controller 31a provides an input signal provided from the joystick 82 to the control device 130. The control device 130 generates position commands based on the received input signal and the rotation angles detected by the encoders E1, and provides the position commands to the servo controllers C1 via the arm controller 31a. The servo controllers C1 generate current commands based on the position commands provided from the arm controller 31a and the rotation angles detected by the encoders E1, and provide the current commands to the servomotors M1. Accordingly, the robot arm 60 is moved in accordance with an operation command provided to the joystick 82.

The control device 130 controls the robot arm 60 based on an input signal from the linear switch 83 of the arm operation unit 80. Specifically, the arm controller 31a provides an input signal provided from the linear switch 83 to the control device 130. The control device 130 generates position commands based on the received input signal and the rotation angles detected by the encoder E1 or E3, and provides the position commands to the servo controller C1 or C3 via the arm controller 31a. The servo controller C1 or C3 generate current commands based on the position commands provided from the arm controller 31a and the rotation angles detected by the encoder E1 or E3, and provide the current commands to the servomotor M1 or M3. Accordingly, the robot arm 60 is moved in accordance with an operation command provided to the linear switch 83.

The medical cart 3 includes the positioner controller 31b. The positioner controller 31b is configured to control the positioner 40 and the medical cart 3. The positioner 40 includes a plurality of servomotors SM, a plurality of encoders EN and a plurality of speed reducers corresponding to a plurality of joints 43 of the positioner 40. The medical cart 3 includes the servo controllers SC configured to control the servomotors SM of the positioner 40. The medical cart 3 includes servomotors SM configured to drive the front wheels of the medical cart 3, the encoders EN, speed reducers, the servo controllers SC, and brakes.

The operation controller 110 is provided in a main body of the remote control apparatus 2. The operation controller 110 is configured to control the operation units 120. The operation controller 110 is associated with both to correspond to the left-hand side operation unit 120 and the right-hand side operation unit 120. The operation unit 120 includes servomotors SM, encoders EN and speed reducers corresponding to the plurality of joints of the operation unit 120. The servo controllers SC configured to control the servomotors SM of the operation unit 120 is provided in the main body of the remote control apparatus 2 adjacent to the operation controller 110.

Detailed Structure of Robot Arm

As shown in FIG. 12, the robot arm 60 includes a first housing 141, a second housing 142 and a third housing 143. The robot arm 60 includes a wiring-line set 150. The first housing 141 and the second housing 142 are configured to pivot with respect to each other by means of the joint 64B as the bend axis. The second housing 142 and the third housing 143 are configured to pivot with respect to each other by means of the joint 64R as the roll axis. The first housing 141, the second housing 142 and the third housing 143 have a cylindrical shape. In other words, the first housing 141, the second housing 142 and the third housing 143 are hollow. The first housing 141, the second housing 142 and the third housing 143 are formed of metal, for example. The rotation axis AX1 is an example of a first rotation axis. The first housing 141 and the second housing 142 are an example of a casing.

Figures 13, 14:
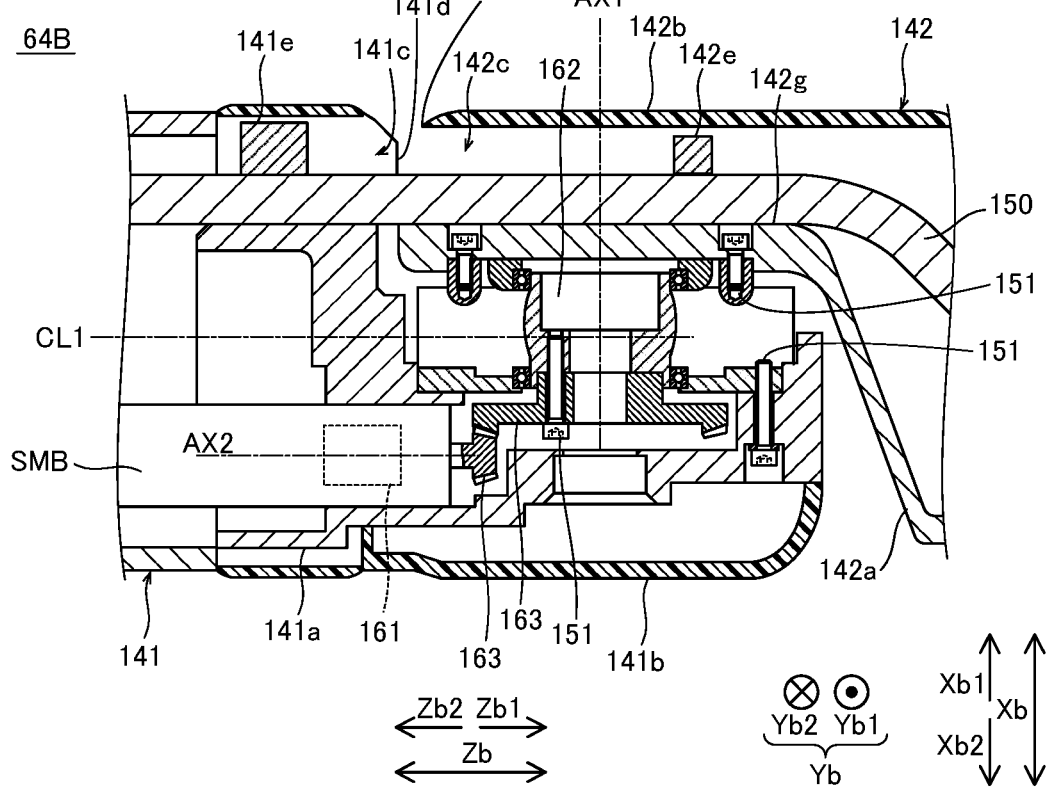
FIG. 13 is a cross-sectional diagram of a bending joint according to the one embodiment as viewed in the Yb direction.
FIG. 14 is a diagram showing speed reduction ratios of joints.

As shown in FIG. 13, the first housing 141 includes a frame part 141a formed of metal, and a cover part 141b formed of resin. A free end side of the first housing 141, which is a part on a Zb1 side of the first housing 141, has a stepped shape. The second housing 142 includes a frame part 142a formed of metal, and a cover part 142b formed of resin. A free end side of the second housing 142, which is a part on a Zb2 side of the second housing 142, has a stepped shape.

Detailed Structure of Bending Joint Corresponding to Bend Axis

The detailed structure of the joint 64B as a bending joint is now described. In this embodiment, as shown in FIG. 13, the joint 64B includes a servomotor SMB, a first speed reducer 161, bevel gears 163 and a second speed reducer 162. The bevel gears 163 are an example of a gear part and a first gear part. The servomotor SMB is an example of an electric motor and a first electric motor.

The servomotor SMB is a relatively small electric motor. For example, the maximum diameter of the servomotor SMB is approximately 35 mm. Also, the servomotor SMB is a high-speed type electric motor. For example, the servomotor SMB can rotate at a speed of not smaller than 7500 rpm. The speed of the servomotor SMB is 10000 rpm, for example. The servomotor SMB is mounted to the frame part 141a of the first housing 141.

In this embodiment, the first speed reducer 161 is configured to reduce a speed of rotation of the servomotor SMB, and to provide the speed-reduced rotation. The first speed reducer 161 includes a planetary speed reducer. The planetary speed reducer includes a planetary gear train. The planetary gear train is a gear assembly including a sun gear having a center axis, and a plurality of planetary gears configured to rotate about their axis while rolling around the sun gear.

In this embodiment, the servomotor SMB and the first speed reducer 161 are integrally formed. A rotation axis AX2 of the servomotor SMB agrees with a rotation axis AX2 of the first speed reducer 161. The servomotor SMB and the first speed reducer 161 are arranged from a Zb2 side to the Zb1 side in this order.

In this embodiment, the bevel gears 163 are configured to further reduce the speed of the rotation provided from the first speed reducer 161, and to provide the further-speed-reduced rotation. The bevel gears 163 are configured to transmit the rotation of the servomotor SMB in a direction orthogonal to the rotation axis AX2 of the servomotor SMB. That is, the rotation axis AX1 of one of the bevel gears 163 is orthogonal to the rotation axis AX2 of the servomotor SMB. The bevel gears 163 are an umbrella gear having a beveled surface. The bevel gears 163 are coupled to the first speed reducer 161 and the second speed reducer 162.

In this embodiment, the second speed reducer 162 is configured to further reduce the speed of the rotation provided from the bevel gears 163, and to provide the further-speed-reduced rotation. The second speed reducer 162 includes at least one of wave gear reducer, an RV speed reducer and a Cyclo drive reducer (registered trademark). The RV speed reducer can be a two-stage speed reducer including a first stage of an eccentric differential type speed reducer, which includes pin gears as inner teeth and a trochoid gear as outer teeth, and a second stage of a spur gear speed reducer. In this embodiment, the second speed reducer 162 is wave gearing speed reducer. The wave gearing refers to a gear assembly including an elliptical gear and a circular gear and to provide differential rotation between them. Wave gear speed reducers are smaller and lighter than RV speed reducers and Cyclo speed reducers (registered trademark). One side of the second speed reducer 162 is coupled to the bevel gears 163 by screws 151 and is mounted to the first housing 141 by the screws 151. Another side of the second speed reducer 162 is mounted to the frame part 142a of the second housing 142 by screws 151.

In this embodiment, a reduction ratio r2 of the second speed reducer 162 shown in FIG. 14 is greater than a reduction ratio r1 of the first speed reducer 161. An available range of the reduction ratio r1 of the first speed reducer 161 is not smaller than 1 and not greater than 15. An available range of the reduction ratio r2 of the second speed reducer 162 is not smaller than 20 and not greater than 200. For example, a ratio r2/r1 between the ratio r2 of the second speed reducer 162 and the ratio r1 of the first speed reducer 161 can be approximately from 7 to 8. The six first speed reducers 161 shown in FIG. 14 have the same reduction ratio, but the speed reducers have different sizes. The six second speed reducers 162 similarly have different sizes.

In this embodiment, reduction ratios between the bevel gears 163 are smaller than the reduction ratio of the second speed reducers 162 and the reduction ratio of the first speed reducers 161. An available range of the reduction ratio r3 between the bevel gears 163 is not smaller than 2 and not greater than 5. For example, a ratio r1/r3 between the ratio r1 of the first speed reducer 161 and the ratio r3 between the bevel gears 163 can be approximately from 1.1 to 3. In FIG. 14, the JT2 axis, the JT4 axis, and the JT6 axis correspond to a bend axis. The gear parts on the JT2 axis, the JT4 axis and the JT6 axis correspond to the bevel gears 163. The bevel gears 163 installed on the JT2 axis, the JT4 axis and the JT6 axis have different sizes and different teeth numbers.

In this embodiment, as shown in FIG. 13, the servomotor SMB, the first speed reducer 161, the bevel gears 163 and the second speed reducer 162 are accommodated in the cylindrical first housing 141. The rotation axis AX2 of the servomotor SMB extends in the Zb direction, which is a longitudinal direction of the cylindrical first housing 141. In the first housing 141, the servomotor SMB, the first speed reducer 161, the bevel gears 163 and the second speed reducer 162 are arranged in this order. The servomotor SMB, the first speed reducer 161 and the bevel gears 163 are aligned in the Zb direction. The second speed reducer 162 is arranged on an Xb1 side of the bevel gears 163.

In this embodiment, the servomotor SMB, the first speed reducer 161 and the bevel gears 163 are arranged in the first housing 141 on one side with respect to a center line CL1 extending in the longitudinal direction of the cylindrical first housing 141 and passing through a center of the first housing 141. The second speed reducer 162 overlaps the center line CL1. The center line CL1 of the first housing 141 is a line that passes through the center in the Xb direction of the first housing 141, and extends in the Zb direction. The servomotor SMB, the first speed reducer 161 and the bevel gears 163 are arranged on the Xb2 side with respect to the center line CL1 in the first housing 141. The second speed reducer 162 straddles the center line CL1. The center line CL1 is an example of a first center line.

That is, in this embodiment, in the joint 64B as a bending joint, the rotation axis AX2 of the servomotor SMB agrees with the rotation axis AX2 of the first speed reducer 161; the rotation axis AX1 of the joint 64B agrees with the rotation axis AX1 of the second speed reducer 162; the rotation axis AX2 of the first speed reducer 161 and the rotation axis AX1 of the second speed reducer 162 are orthogonal to each other; and the bevel gears 163 transmit rotation of the first speed reducer into a direction orthogonal to the rotation axis AX2 of the first speed reducer 161.

Detailed Structure of Twisting Joint Corresponding to Roll Axis

Figure 15:
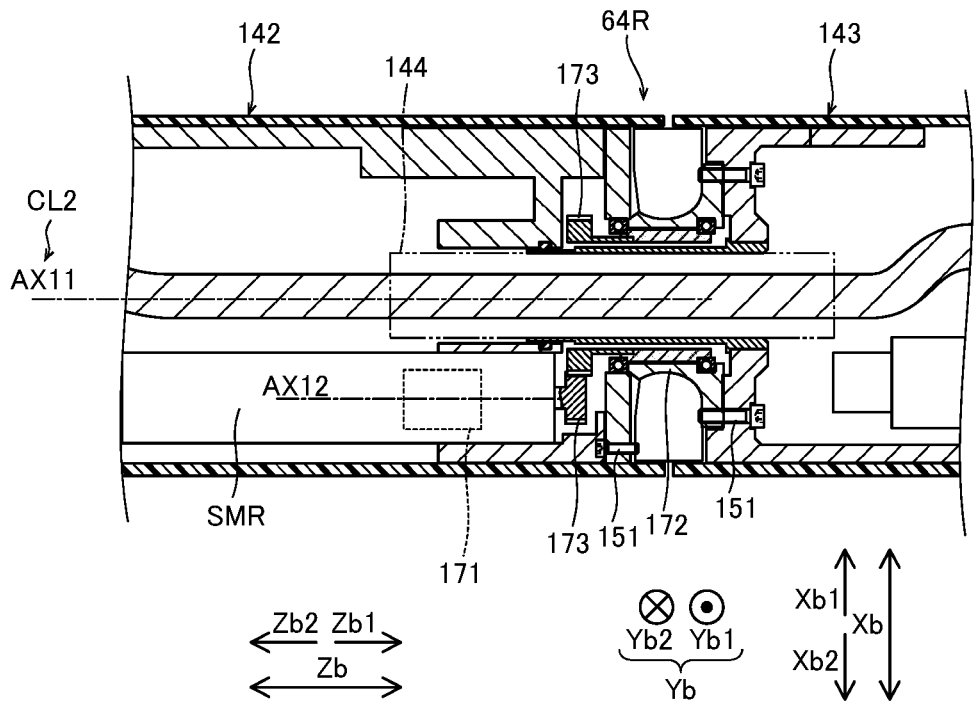
FIG. 15 is a cross-sectional diagram of a twisting joint according to the one embodiment as viewed in the Yb direction.

The detailed structure of the joint 64R as a twisting joint is now described. In this embodiment, as shown in FIG. 15, the joint 64R includes a servomotor SMR, a first speed reducer 171, helical gears 173 and a second speed reducer 172. The first speed reducer 171 and the second speed reducer 172 are an example of a third speed reducer and an example of a fourth speed reducer, respectively. The helical gears 173 are an example of a gear part and a second gear part. The servomotor SMR is an example of an electric motor and a second electric motor. The helical gear is sometimes referred to as a skew gear or a helical tooth gear.

The servomotor SMR is arranged in the second housing 142. The servomotor SMB has a configuration similar to the servomotor SMR.

In this embodiment, the first speed reducer 171 is configured to reduce a speed of rotation of the servomotor SMR, and to provide the speed-reduced rotation. The servomotor SMR and the first speed reducer 171 are integrally formed. The first speed reducer 171 includes a planetary speed reducer. The first speed reducer 171 has a configuration similar to the first speed reducer 161.

In this embodiment, the helical gears 173 are configured to further reduce the speed of the rotation provided from the first speed reducer 171, and to provide the further-speed-reduced rotation. The helical gears 173 are configured to transmit the rotation of the servomotor SMR in a direction in parallel to the rotation axis AX12 of the servomotor SMR. The helical gears 173 are coupled to the first speed reducer 171 and the second speed reducer 172.

In this embodiment, the second speed reducer 172 is configured to further reduce the speed of the rotation provided from the helical gears 173, and to provide the further-speed-reduced rotation. One side of the second speed reducer 172 is coupled to the helical gears 173 and is mounted to the second housing 142 by screws 151. Another side of the second speed reducer 172 is mounted to the third housing 143 by screws 151. The second speed reducer 172 includes at least one of wave gear reducer, an RV speed reducer and a Cyclo drive reducer (registered trademark).

In this embodiment, a reduction ratio r2 of the second speed reducer 172 shown in FIG. 14 is greater than a reduction ratio r1 of the first speed reducer 171. An available range of the reduction ratio r1 of the first speed reducer 171 is not smaller than 1 and not greater than 15. An available range of the reduction ratio r2 of the second speed reducer 172 is not smaller than 20 and not greater than 200. For example, r2/r1 between the ratio r2 of the second speed reducer 172 and the ratio r1 of the first speed reducer 171 can be approximately from 7 to 8. In FIG. 14, the JT1 axis, the JT3 axis, and the JT5 axis correspond to a roll axis. The gear parts on the JT1 axis, the JT3 axis and the JT5 axis correspond to the helical gears 173. The helical gears 173 installed on the JT1 axis, the JT3 axis and the JT5 axis have different sizes and different teeth numbers.

In this embodiment, reduction ratios of the helical gears 173 are smaller than the reduction ratio of the second speed reducers 172 and the reduction ratio of the first speed reducers 171. An available range of the reduction ratio r3 between the helical gears 173 is not smaller than 2 and not greater than 3. For example, a ratio r1/r3 between the ratio r1 of the first speed reducer 171 and the ratio r3 between the helical gears 173 can be approximately from 1.1 to 3. As shown in FIG. 14, the helical gears 173 have different sizes and different teeth numbers.

In this embodiment, as shown in FIG. 15, the servomotor SMR, the first speed reducer 171, the helical gears 173 and the second speed reducer 172 are accommodated in the cylindrical second housing 142. The rotation axis AX12 of the servomotor SMR extends in the Zb direction, which is a longitudinal direction of the cylindrical second housing 142. In the second housing 142, the servomotor SMR, the first speed reducer 171, the helical gears 173 and the second speed reducer 172 are arranged in this order. The servomotor SMB, the first speed reducer 171, the helical gears 173 and the second speed reducer 172 are aligned in the Zb direction.

In this embodiment, the servomotor SMR, the first speed reducer 171 and one of the helical gears 173 are arranged in the second housing 142 on one side with respect to the center line CL2 extending in the longitudinal direction of the cylindrical second housing 142 and passing through a center of the second housing 142. Another of the helical gears 173 and the second speed reducer 172 overlap the center line CL2 of the second housing 142. The center line CL2 of the second housing 142 is a line that passes through the center in the Xb direction and the Yb direction of the second housing 142, and extends in the Zb direction. The servomotor SMR, the first speed reducer 171, and the rotation axis AX12 of one of the helical gears 173 are arranged on the Xb2 side with respect to the center line CL2 in the second housing 142. The rotation axis AX11 is an example of a second rotation axis. The center line CL2 is an example of a second center line.

In this embodiment, as shown in FIG. 14, the plurality of first speed reducers 161 and the plurality of first speed reducers 161 in the plurality of joints 64 have a common speed reduction ratio r1. The plurality of second speed reducers 162 and the plurality of second speed reducers 172 in the plurality of joints 64 have a common speed reduction ratio r2. The bevel gear sets 163 and the helical gear sets 173 have different speed reduction ratios r3. As a result, the total reduction ratios r4 of the joints 64 are adjusted. In other words, speed reduction ratios r3a, r3b, r3c, r3d, r3e and r3f of the bevel gear sets 163 and the helical gear sets 173 are different from each other. Consequently, total gear ratios r4a, r4b, r4c, r4d, r4e and r4f of the joints 64 are adjusted.

That is, in this embodiment, the joint 64R is a twisting joint; the rotation axis AX12 of the servomotor SMR agrees with the rotation axis AX12 of the first speed reducer 171; the rotation axis AX11 of the joint 64R agrees with the rotation axis AX11 of the second speed reducer 172; the rotation axis AX12 of the first speed reducer 171 and the rotation axis AX11 of the second speed reducer 172 are parallel to each other; and the helical gears 173 transmit rotation of the first speed reducer into a direction parallel to the rotation axis AX12 of the first speed reducer 171.

Wiring-Line Set

As shown in FIG. 13, the wiring-line set 150 is accommodated in the joint 64B in this embodiment. The wiring-line set 150 is arranged in the robot arm 60 so that the wiring-line set 150 extends in the longitudinal direction of the robot arm 60, and passes through the rotation axis AX1 of the joint 64B and through an AX1-Yb plane orthogonal to the longitudinal direction of the robot arm 60. Irrespective of a non-bent state of the robot arm 60 in which the first housing 141 and the second housing 142 extend in the Zb direction or a bent state of the robot arm 60 in which the first housing 141 and the second housing 142 intersect each other, the wiring-line set 150 is held while keeping passing through the rotation axis AX1 of the joint 64B and through the AX1-Yb plane orthogonal to the longitudinal direction of the robot arm 60. The rotation axis AX1 of the joint 64B is also the rotation axis AX1 of the second speed reducer 162. The wiring-line set 150 includes power and signal lines. In a case in which a concept that an object is orthogonal to the rotation axis AX1 is stated, the concept includes that the object intersects the rotation axis AX1 at 90 degrees and that the object intersects the rotation axis AX1 at an angle around degrees.

In this embodiment, the wiring-line set 150 extends from an interior of the first housing 141 to an interior of the second housing 142. Specifically, the first housing 141 includes a first opening 141c. The second housing 142 includes a second opening 142c. The wiring-line set 150 passes through the first opening 141c and the second opening 142c. In the bent state of the robot arm 60 in which the first housing 141 and the second housing 142 intersect each other, the first opening 141c opens toward the Zb1 side. In the non-bent state of the robot arm 60 in which the first housing 141 and the second housing 142 extend in the Zb direction, the first opening 141c opens also toward the Zb1 side. The first opening 141c is formed in the Yb direction. The second opening 142c opens toward the Zb2 side. The second opening 142c is formed in the Yb direction. The first opening 141c and the second opening 142c face each other.

In this embodiment, the first opening 141c and the second opening 142c are spaced away from each other in the longitudinal direction of the robot arm 60. In the non-bent state of the robot arm 60 in which the first housing 141 and the second housing 142 extend in the Zb direction, the first opening 141c and the second opening 142c are spaced away from each other in the Zb direction. Irrespective of the non-bent state of the robot arm 60 or the bent state of the robot arm 60, the first opening 141c and the second opening 142c are spaced away from each other. Accordingly, an end 141d on the Zb1 side of the first housing 141 does not interfere with an end 142d on the Zb2 side of the second housing 142.

Figure 16:
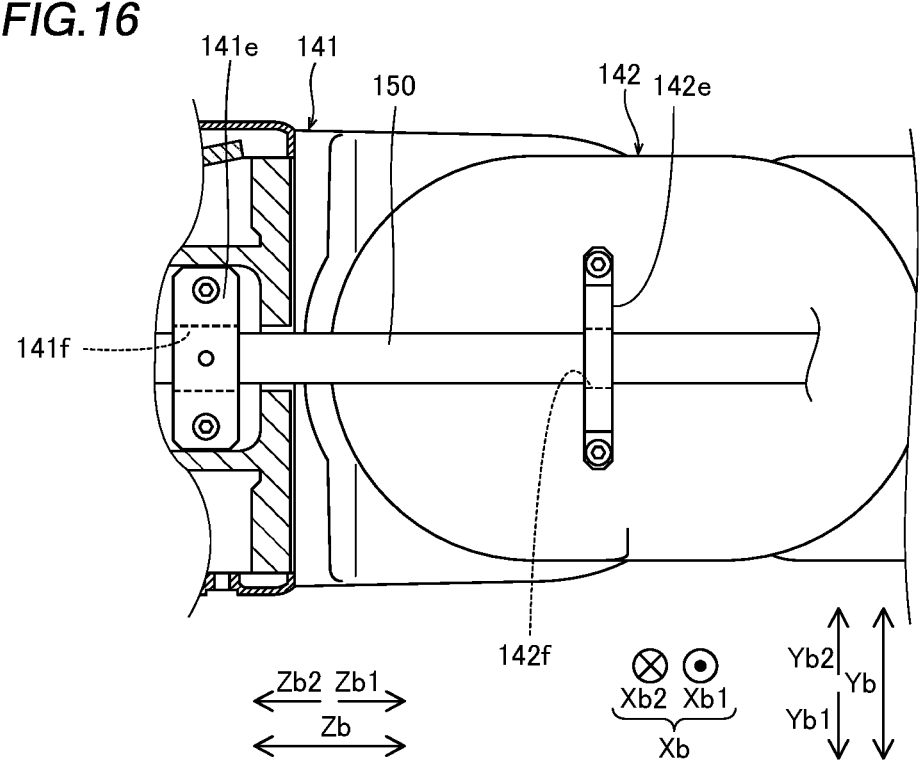
FIG. 16 is a cross-sectional diagram of a bending joint according to the one embodiment as viewed in an Xb direction.
Figure 17:
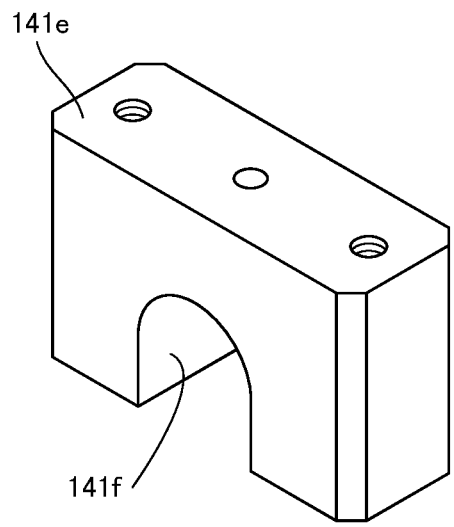
FIG. 17 is a perspective view of a first limiter according to the one embodiment.

In this embodiment, as shown in FIG. 16, the first housing 141 includes a first limiter 141e configured to limit movement of the wiring-line set 150 extending from the second housing 142. As shown in FIG. 17, the first limiter 141e has a roughly U shape. The wiring-line set 150 is held in a cutout part 141f formed between legs of the roughly U-shaped first limiter 141e. The wiring-line set 150 is in contact with the cutout part 141f. This contact limits movement of the wiring-line set 150 in the Yb direction. The first limiter 141e is mounted to the frame part 141a of the first housing 141 by screws, etc. The first opening 141c is formed of a gap between the frame part 141a and the cover part 141b. The first limiter 141e is arranged between the frame part 141a and the cover part 141b.

Figure 18:
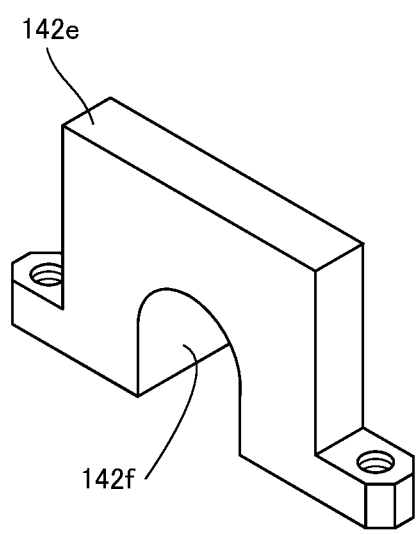
FIG. 18 is a perspective view of a second limiter according to the one embodiment.

In this embodiment, as shown in FIG. 16, the second housing 142 includes a second limiter 142e configured to limit movement of the wiring-line set 150 extending from the first housing 141. As shown in FIG. 18, the second limiter 142e has a roughly U shape. The wiring-line set 150 is held in a cutout part 142f formed between legs of the roughly U-shaped second limiter 142e. The wiring-line set 150 is in contact with the cutout part 142f. This contact limits movement of the wiring-line set 150 in the Yb direction. As shown in FIG. 13, the second limiter 142e is mounted to the frame part 142a of the second housing 142.

In this embodiment, the servomotor SMB is arranged in the first housing 141 on the Xb2 side with respect to the center line CL1 extending in the longitudinal direction of the first housing 141 and passing through the center of the first housing 141. The second speed reducer 162 overlaps the center line CL1, and the wiring-line set 150 is arranged on the Xb1 side with respect to the center line CL1. The first speed reducer 161 and the bevel gears 163 are arranged on the Xb2 side with respect to the center line CL1 of the first housing 141.

In this embodiment, as shown in FIG. 15, the second speed reducer 172 of the joint 64R is hollow. In the joint 64R, the wiring-line set 150 is held in the robot arm 60 so that the wiring-line set passes through an interior of the second speed reducer 172. The wiring-line set 150 passes through the second speed reducer 172, and then extends from the second housing 142 to the third housing 143.

In this embodiment, a cylindrical wiring-line set protector 144 is provided. The wiring-line set protector 144 is arranged in the hollow second speed reducer 172, and receives the wiring-line set 150. The wiring-line set protector 144 is formed of an elastic material. The wiring-line set protector 144 is formed of a resin, for example. The wiring-line set protector 144 extends from the second housing 142 to the third housing 143. The wiring-line set protector 144 is not necessarily provided.

Advantages of the Embodiment

The joint 64B, which is a bending joint, includes a servomotor SMB, a first speed reducer 161 configured to reduce a speed of rotation of the servomotor SMB, and to provide the speed-reduced rotation, bevel gears 163 configured to further reduce the speed of the rotation provided from the first speed reducer 161, and to provide the further-speed-reduced rotation, and a second speed reducer 162 configured to reduce the further-speed-reduced rotation provided from the bevel gears 163. According to this configuration, because a speed of rotation of the servomotor SMB is reduced by the first speed reducer 161, the bevel gear set 163 and the second speed reducer 162 as three parts, a total gear ratio r4 of the joint 64B can be large as compared with a case such a joint has one speed reducer. Accordingly, even in a case in which a small servomotor SMB is used, a desired torque to rotate the joint 64B can be provided. Consequently, because the robot arm 60 does not necessarily have a large servomotor SMB, the robot arm 60 can be thinned. The joint 64R, which is a twisting joint, can have a similar effect.

A speed reduction ratio r2 of the second speed reducer 162 is greater than a speed reduction ratio r1 of the first speed reducer 161. Accordingly, because backlash of the second speed reducer 162, which serves as an output side of the rotation in joint 64B, can be relatively small, rotation of the joint 64B can be precisely controlled. Also, because the reduction ratio r1 of the first speed reducer 161 is relatively small, transmission of an excessively large torque from the first speed reducer 161 to the bevel gears 163 can be prevented. For this reason, mechanical strength of the bevel gears 163 is not necessarily excessively increased, which means that the gear part with high mechanical strength is not required, and as a result freedom of choice of the bevel gears 163 can be increased. The joint 64R can have a similar effect.

The first speed reducers 161 includes a planetary speed reducer, and the second speed reducer 162 includes at least one of wave gear reducer, an RV speed reducer and a Cyclo drive reducer (registered trademark). Because planetary speed reducers are relatively small in general, the first speed reducer 161 can be easily downsized. Consequently, the combination of the small servomotor SMB and the small first speed reducer 161 can further thin the robot arm 60. Also, wave gear reducers, RV reducers, and cyclo speed reducers (registered trademark) have a relatively high reduction ratio in general, the reduction ratio r2 of the second speed reducers 162 can be easily increased. The joint 64R can have a similar effect.

A ratio r3 between the bevel gears 163 is smaller than the ratio r2 of the second speed reducer 162 and the ratio r1 of the first speed reducer 161. Accordingly, size increase of the bevel gears 163 can be prevented as compared with a case in which the reduction ratio r3 is increased by increasing sizes of the bevel gears 163. This can also thin the robot arm 60. Note that, the helical gears 173 of the joint 64R can have a similar effect.

The servomotor SMB and the first speed reducer 161 are integrally formed. Accordingly, dissimilar to a case in which the servomotor SMB and the first speed reducer 161 are separately formed, the servomotor SMB and the first speed reducer 161 can be installed onto the robot arm 60 by one process. Accordingly, the installation process of the servomotor SMB and the first speed reducer 161 can be simple. The joint 64R can have a similar effect.

The rotation axis of the servomotor SMB extends in the longitudinal direction of the cylindrical first housing 141. In general, a longitudinal direction of a servomotor SMB corresponds to a rotation axis AX2. According to the configuration in which the rotation axis AX2 of the servomotor SMB extends in the Zb direction, which is the longitudinal direction of the cylindrical first housing 141, the robot arm 60 can be further thinned as compared with a case in which the rotation axis AX2 of the servomotor SMB extends in a thickness direction of the robot arm 60, which is orthogonal to the longitudinal direction of the cylindrical first housing 141, The joint 64R can have a similar effect.

The bevel gears 163 are configured to transmit the rotation of the servomotor SMB in a direction orthogonal to a rotation axis direction of the servomotor SMB. Accordingly, the rotation of the servomotor SMB can be easily transmitted by the bevel gears 163 in a direction orthogonal to the rotation axis direction of the servomotor SMB.

The servomotor SMB, the first speed reducer 161 and the bevel gears 163 are arranged in the first housing 141 on one side with respect to the center line CL1 extending in the Zb direction, which is the longitudinal direction of the cylindrical first housing 141, and passing through a center of the first housing 141, and the second speed reducer 162 overlaps the center line CL1. Accordingly, because the servomotor SMB, the first speed reducer 161 and the bevel gears 163 are arranged close to an end side of the first housing 141, sufficient space can be provided in the first housing 141 to accommodate the second speed reducer 162.

The helical gears 173 are configured to transmit the rotation of the servomotor SMB in the Zb direction in parallel to the rotation axis AX12 of the servomotor SMR. Accordingly, the rotation of the servomotor SMB can be easily transmitted by the helical gears 173 in the Zb direction in parallel to the rotation axis AX12 of the servomotor SMR.

The servomotor SMR, the first speed reducer 171 and one of the helical gears 173 are arranged in the second housing 142 on one side with respect to the center line CL2 extending in the longitudinal direction of the cylindrical second housing 142, and passing through the center of the second housing 142, and another of the helical gears 173 and the second speed reducer 172 overlap the center line CL2 of the second housing 142. Accordingly, because the servomotor SMR, the first speed reducer 171 and one of the helical gears 173 are arranged close to an end side of the second housing 142, the second speed reducer 172 can be easily arranged to overlap the center line CL2 of the second housing 142. In addition, because the second speed reducer 172 overlaps the center line CL2 of the second housing 142 so that the rotational axis AX11 of the second speed reducer 172 agrees with the center line CL2 of the cylindrical second housing 142, the cylindrical second housing 142 can rotate without decentering.

The first speed reducers 161 of the plurality of joints 64B have a common speed reduction ratio r1; the second speed reducers 162 of the plurality of joints 64B have a common speed reduction ratio r2; and the bevel gear sets 163 of the plurality of joints 64B have reduction ratios r3 different from each other. As a result, the total reduction ratios r4 of the joints 64B are adjusted. Consequently, because common first speed reducers 161 and common second speed reducers 162 can be used in the plurality of joints 64B, the number of types of components that make up the robot arm 60 can be prevented from increasing. The joint 64R can have a similar effect.

In the joint 64B according to this embodiment, which is a bending joint, the rotation axis AX2 of the servomotor SMB agrees with the rotation axis AX2 of the first speed reducer 161; the rotation axis AX1 of the joint 64B agrees with the rotation axis AX1 of the second speed reducer 162; the rotation axis AX2 of the first speed reducer 161 and the rotation axis AX1 of the second speed reducer 162 are orthogonal to each other; and the bevel gears 163 transmit rotation of the first speed reducer into a direction orthogonal to the rotation axis AX2 of the first speed reducer 161. According to this configuration, because a speed of rotation of the servomotor SMB is reduced by the first speed reducer 161, the bevel gear set 163 and the second speed reducer 162 as three parts, a desired torque to rotate the joint 64B can be provided by even a small servomotor SMB, and as a result the robot arm 60 can be thinned.

In this embodiment, the joint 64R is a twisting joint; the rotation axis AX12 of the servomotor SMR agrees with the rotation axis AX12 of the first speed reducer 171; the rotation axis AX11 of the joint 64R agrees with the rotation axis AX11 of the second speed reducer 172; the rotation axis AX12 of the first speed reducer 171 and the rotation axis AX11 of the second speed reducer 172 are parallel to each other; and the helical gears 173 transmit rotation of the first speed reducer into a direction parallel to the rotation axis AX12 of the first speed reducer 171. According to this configuration, because a speed of rotation of the servomotor SMR is reduced by the first speed reducer 171, the helical gear set 173 and the second speed reducer 172 as three parts, a desired torque to rotate the joint 64R can be provided by even a small servomotor SMR, and as a result the robot arm 60 can be thinned.

Modified Embodiment

Note that the embodiment disclosed this time must be considered as illustrative in all points and not restrictive. The scope of the present invention is not shown by the above description of the embodiments but by the scope of claims for patent, and all modifications or modified examples within the meaning and scope equivalent to the scope of claims for patent are further included.

While the example in which a reduction ratio r2 of the second speed reducer 162 greater than a reduction ratio r2 of the first speed reducer 161 has been shown in the aforementioned embodiment, the present disclosure is not limited to this. In the present disclosure, the speed reduction ratio r2 of the second speed reducer 162 may be similar the speed reduction ratio r1 of the first speed reducer 161. This may be applied to the second speed reducer 172 and the first speed reducer 171 of the joint 64R.

While the example in which the first speed reducer 161 and the first speed reducer 171 are a planetary speed reducer has been shown in the aforementioned embodiment, the present disclosure is not limited to this. In the present disclosure, the first speed reducer 161 and the first speed reducer 171 may be a speed reducer other than planetary reducer.

While the example in which a reduction ratio r3 between the bevel gears 163 is smaller than the reduction ratio r2 of the second speed reducer 162 and the reduction ratio r1 of the first speed reducer 161 has been shown in the aforementioned embodiment, the present disclosure is not limited to this. In the present disclosure, the ratio r3 between the bevel gears 163 may be greater than the ratio r2 of the second speed reducer 162 and the ratio r1 of the first speed reducer 161. This may be applied to the helical gears 173 of the joint 64R.

While the example in which the servomotor SMB and the first speed reducer 161 are integrally formed has been shown in the aforementioned embodiment, the present disclosure is not limited to this. In the present disclosure, the servomotor SMB and the first speed reducer 161 may be separately formed. This may be applied to the servomotor SMR and the first speed reducer 171 of the joint 64R.

While the example in which the bevel gears 163 are used as a gear part that is configured to transmit rotation of the servomotor SMB in a direction orthogonal to the rotation axis AX2 of the servomotor SMB has been shown in the aforementioned embodiment, the present disclosure is not limited to this. In the present disclosure, a gear part other than the bevel gears 163 may be used as the gear part configured to transmit rotation of the servomotor SMB in a direction orthogonal to the rotation axis AX2 of the servomotor SMB.

While the example in which the helical gears 173 are used as a gear part that is configured to transmit rotation of the servomotor SMR in a direction in parallel to the rotation axis AX12 of the servomotor SMR has been shown in the aforementioned embodiment, the present disclosure is not limited to this. In the present disclosure, a gear part other than the helical gears 173 may be used as the gear part configured to transmit rotation of the servomotor SMR in a direction in parallel to the rotation axis AX12 of the servomotor SMR.

While the example in which the first speed reducers 161 of the plurality of joints 64B have a common speed reduction ratio r1 has been shown in the aforementioned embodiment, the present disclosure is not limited to this. In the present disclosure, the first speed reducers 161 of the plurality of joints 64B may have different speed reduction ratios r1. This may be applied to the second speed reducer 162, the first speed reducer 171 and the second speed reducer 172.

While the example in which the bevel gear sets 163 of the plurality of joints 64B have reduction ratios r3 different from each other has been shown in the aforementioned embodiment, the present disclosure is not limited to this. The bevel gear sets 163 of the plurality of joints 64B may have a common reduction ratio r3. This may be applied to the helical gear sets 173.

While the example in which four robot arms 60 are provided has been shown in the aforementioned embodiment, the present disclosure is not limited to this. In the present disclosure, any number of robot arms 60 may be provided as long as at least one robot arms are provided.

While the example in which the arms 61 and the positioner 40 are constructed of a 7-axis multi-joint robot has been shown in the aforementioned embodiment, the present disclosure is not limited to this. For example, the arms 61 and the positioner 40 are constructed of a multi-joint robot having an axis configuration other than the 7-axis multi-joint robot. The multi-joint robot having an axis configuration other than the 7-axis multi-joint robot can be a 6-axis or 8-axis multi-joint robot, for example.

While the example in which the surgical robot 1 includes the medical cart 3, the positioner 40 and the arm base 50 has been shown in the aforementioned embodiment, the present disclosure is not limited to this. The medical cart 3, the positioner 40 and the arm base 50 are not necessarily provides, and the surgical robot 1 may include only the robot arms 60, for example.

Figure 19:
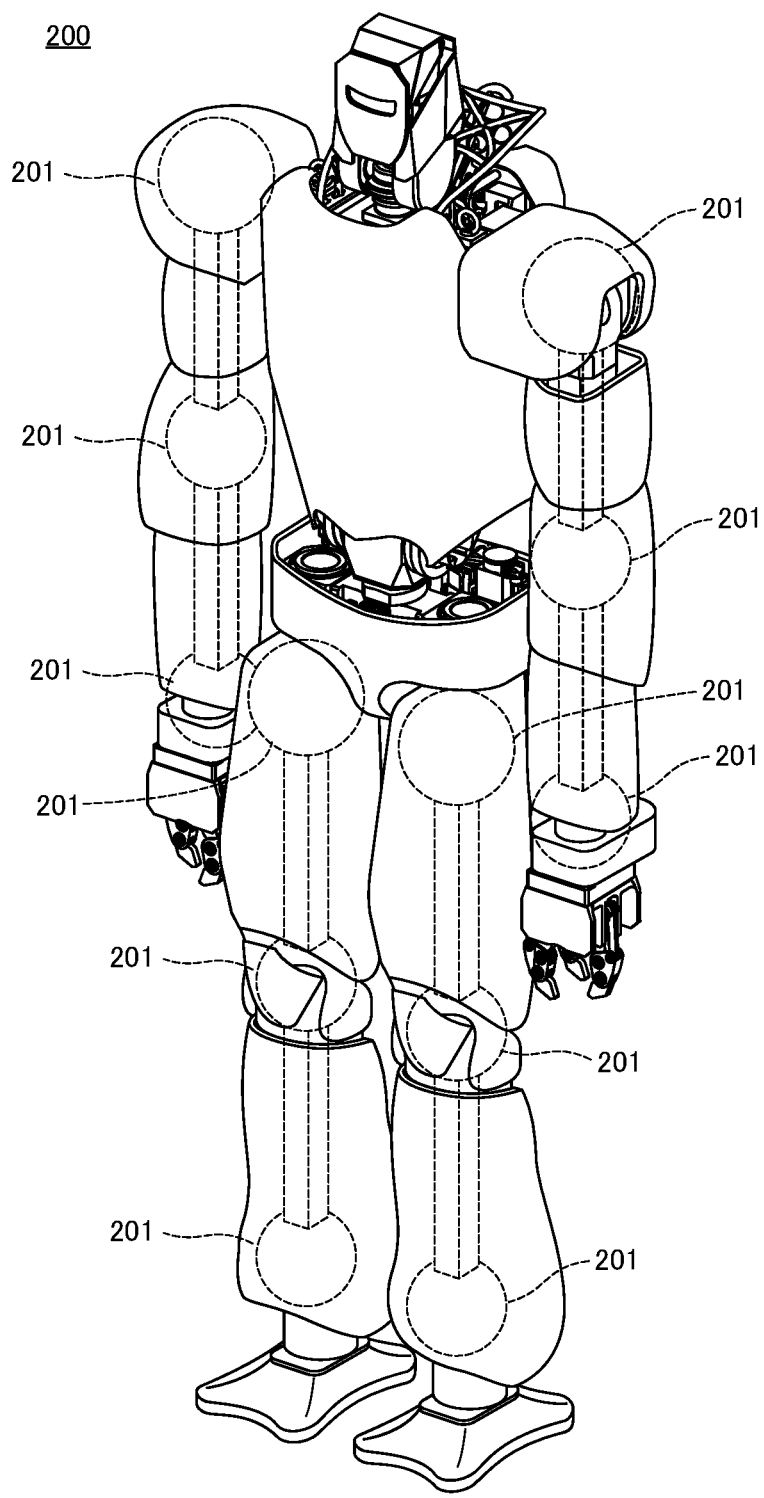
FIG. 19 is a diagram showing a humanoid robot according to a modified example.

While the example in which the present disclosure is applied to the surgical robot 1 has been shown in the aforementioned embodiment, the present disclosure is not limited to this. For example, the present disclosure may be applied to joints 201 of a humanoid robot 200 as shown in FIG. 19.

What is claimed is:

1. A surgical robot comprising:
a robot arm including a free end to which a surgical instrument is attached, and a joint or joints, wherein
the joint or joints include
an electric motor,
a first speed reducer configured to reduce a speed of rotation of the electric motor, and to provide the speed-reduced rotation,
a gear part configured to further reduce the speed of the rotation provided from the first speed reducer, and to provide the further-speed-reduced rotation, and
a second speed reducer configured to reduce the further-speed-reduced rotation provided from the gear part, wherein
the joint or joints include a second joint configured to rotate about a longitudinal direction of the robot arm as a second rotation axis; and
the gear part includes helical gears configured to transmit the rotation of the electric motor in a direction parallel to the rotation axis direction of the electric motor.

2. The surgical robot according to claim 1, wherein a speed reduction ratio of the second speed reducer is greater than a speed reduction ratio of the first speed reducer.

3. The surgical robot according to claim 2, wherein
the first speed reducer includes a planetary speed reducer; and
the second speed reducer includes at least one of wave gear reducer, an RV speed reducer and a Cyclo drive reducer (registered trademark).

4. The surgical robot according to claim 2, wherein a speed reduction ratio of the gear part is smaller than the speed reduction ratio of the second speed reducer and the speed reduction ratio of the first speed reducer.

5. The surgical robot according to claim 1, wherein the electric motor and the first speed reducer are formed integrally with each other.

6. The surgical robot according to claim 1, wherein
the robot arm further includes a cylindrical housing that accommodates the electric motor, the first speed reducer, the gear part, and the second speed reducer; and
a rotation axis of the electric motor extends in a longitudinal direction of the cylindrical housing.

7. The surgical robot according to claim 1, wherein the joint or joints include a first joint configured to rotate about a first rotation axis to be able to bend the robot arm; and
the gear part includes bevel gears configured to transmit the rotation of the electric motor in a direction orthogonal to a rotation axis direction of the electric motor.

8. The surgical robot according to claim 7, wherein the robot arm further includes a cylindrical first housing that accommodates the electric motor, the first speed reducer, the bevel gears, and the second speed reducer;
the electric motor, the first speed reducer and the gear part are arranged in the first housing on one side with respect to the first center line extending in a longitudinal direction of the cylindrical first housing and passing through a center of the first housing; and
the second speed reducer overlaps the first center line.

9. The surgical robot according to claim 1, wherein the robot arm further includes a cylindrical second housing that accommodates the electric motor, the first speed reducer, the helical gears, and the second speed reducer;
the electric motor, the first speed reducer and one of the helical gears are arranged in the second housing on one side with respect to a second center line extending in a longitudinal direction of the cylindrical second housing and passing through a center of the second housing; and
another of the helical gears and the second speed reducer overlaps the second center line of the second housing.

10. A surgical robot comprising:
a robot arm including a free end to which a surgical instrument is attached, and a joint or joints, wherein
the joint or joints include
an electric motor,
a first speed reducer configured to reduce a speed of rotation of the electric motor, and to provide the speed-reduced rotation,
a gear part configured to further reduce the speed of the rotation provided from the first speed reducer, and to provide the further-speed-reduced rotation, and
a second speed reducer configured to reduce the further-speed-reduced rotation provided from the gear part, wherein
a plurality of joints are provided as the joint or joints in the robot arm,
the first speed reducers of the plurality of joints have a common speed reduction ratio,
the second speed reducers of the plurality of joints have a common speed reduction ratio, and
the gear parts of the plurality of joints have reduction ratios different from each other.

11. A surgical robot comprising:
a robot arm including a free end to which a surgical instrument is attached, and a joint or joints, wherein
the joint or joints include
an electric motor,
a first speed reducer configured to reduce a speed of rotation of the electric motor, and to provide the speed-reduced rotation,
a gear part configured to further reduce the speed of the rotation provided from the first speed reducer, and to provide the further-speed-reduced rotation, and a second speed reducer configured to reduce the further-speed-reduced rotation provided from the gear part, wherein
the joint is a bending joint,
a rotation axis of the electric motor agrees with a rotation axis of the first speed reducer,
a rotation axis of the bending joint agrees with a rotation axis of the second speed reducer,
the rotation axis of the first speed reducer and the rotation axis of the second speed reducer are orthogonal to each other, and
the gear part transmits rotation of the first speed reducer into a direction orthogonal to the rotation axis of the first speed reducer.

12. A surgical robot according to claim 1, comprising:
a robot arm including a free end to which a surgical instrument is attached, and a joint or joints, wherein the joint or joints include
an electric motor,
a first speed reducer configured to reduce a speed of rotation of the electric motor, and to provide the speed-reduced rotation,
a gear part configured to further reduce the speed of the rotation provided from the first speed reducer, and to provide the further-speed-reduced rotation, and a second speed reducer configured to reduce the further-speed-reduced rotation provided from the gear part, wherein
the joint is a twisting joint,
a rotation axis of the electric motor agrees with a rotation axis of the first speed reducer,
a rotation axis of the twisting joint agrees with a rotation axis of the second speed reducer,
the rotation axis of the first speed reducer and the rotation axis of the second speed reducer are parallel to each other, and
the gear part transmits rotation of the first speed reducer into a direction parallel to the rotation axis of the first speed reducer.

13. A surgical robot comprising a robot arm including a fore end to which a surgical instrument is attached, and bending and twisting joints, wherein
the bending joint includes
a first electric motor,
a first speed reducer configured to reduce a speed of rotation of the first electric motor, and to provide the speed-reduced rotation,
a first gear part configured to further reduce the speed of the rotation provided from the first speed reducer, and to provide the further-speed-reduced rotation, and
a second speed reducer configured to reduce the further-speed-reduced rotation provided from the first gear part, and the twisting joint includes
a second electric motor,
a third speed reducer configured to reduce a speed of rotation of the second electric motor, and to provide the speed-reduced rotation,
a second gear part configured to further reduce the speed of the rotation provided from the third speed reducer, and to provide the further-speed-reduced rotation, and
a fourth speed reducer configured to reduce the further-speed-reduced rotation provided from the second gear part.

14. The surgical robot according to claim 13, wherein each of the first and third speed reducers includes a planetary speed reducer;
the first gear part includes bevel gears;
the second gear part includes helical gears; and
each of the second and fourth speed reducers includes at least one of wave gearing reducer, an RV speed reducer and a Cyclo drive reducer (registered trademark).

15. The surgical robot according to claim 13, wherein a speed reduction ratio of the second speed reducer is greater than a speed reduction ratio of the first speed reducer, a speed reduction ratio of the fourth speed reducer is greater than a speed reduction ratio of the third speed reducer.

16. The surgical robot according to claim 15 further comprising each of the first and third speed reducers includes a planetary speed reducer, wherein
each of the second and fourth speed reducers includes at least one of wave gearing reducer, an RV speed reducer and a Cyclo drive reducer (registered trademark).

17. The surgical robot according to claim 15, wherein a speed reduction ratio of the first gear part is smaller than a speed reduction ratio of the first speed reducer, and a speed reduction ratio of the second gear part is smaller than a speed reduction ratio of the third speed reducer.

18. The surgical robot according to claim 17, wherein the first gear part includes bevel gears, and the second gear part includes helical gears.

* * * * *